US012728080B2

(12) United States Patent
Pang et al.

(10) Patent No.: US 12,728,080 B2
(45) Date of Patent: Sep. 8, 2026

(54) COSMETIC KIT WITH A CLEANSING STICK, DISPENSING CONTAINER, AND CUTTING DEVICE

(71) Applicant: L'OREAL, Paris (FR)

(72) Inventors: Christopher Pang, New York, NY (US); Mariko Hasebe, New York, NY (US); Changlong Chen, Edison, NJ (US)

(73) Assignee: L'OREAL, Paris (FR)

( * ) Notice: Subject to any disclaimer, the term of this patent is extended or adjusted under 35 U.S.C. 154(b) by 246 days.

(21) Appl. No.: 18/757,209

(22) Filed: Jun. 27, 2024

(65) Prior Publication Data

US 2026/0000583 A1 Jan. 1, 2026

(51) Int. Cl.
*A61K 8/04* (2006.01)
*A45D 40/00* (2006.01)
*A61Q 9/02* (2006.01)

(52) U.S. Cl.
CPC .......... *A61K 8/042* (2013.01); *A45D 40/0081* (2013.01); *A61Q 9/02* (2013.01); *A45D 2200/25* (2013.01); *A61K 2800/30* (2013.01); *A61K 2800/87* (2013.01); *A61K 2800/88* (2013.01)

(58) Field of Classification Search
CPC ...................................................... A61K 8/042
USPC ......................................................... 424/401
See application file for complete search history.

(56) References Cited

U.S. PATENT DOCUMENTS 10,028,895 B2 7/2018 Bergeron et al.
10,045,917 B2 8/2018 Lu et al.
10,813,852 B2 10/2020 Sverdlove et al.
11,253,112 B1 2/2022 Bickford et al.
11,701,317 B2 7/2023 Liu et al.
2004/0005283 A1* 1/2004 Cernasov .............. A61K 8/042 424/63
2013/0225472 A1 8/2013 Wu et al.
2014/0127375 A1 5/2014 Cao et al.
(Continued)

FOREIGN PATENT DOCUMENTS

CN 109966184 B 9/2021

OTHER PUBLICATIONS

International Search Report and Written Opinion issued on Sep. 26, 2025 for corresponding PCT Application No. PCT/US2025/028293.
(Continued)

*Primary Examiner* — Walter E Webb
(74) *Attorney, Agent, or Firm* — POLSINELLI PC

(57) ABSTRACT

A cosmetic kit is disclosed having a container and a shaving cap. The container comprises interior chamber containing a solidified gel of a micellar solution and a dispensing opening that exposes an outer surface of the solidified gel. The exposed surface of the solidified gel to a surface, like skin, and can be cleaned with the shaving cap, which removes at least a portion of the exposed surface of the solidified gel. The shaving cap comprises a planer surface and one or more openings or slits through the planar surface having shaving edges that shave the exposed surface of the solidified gel when applied against the exposed surface, for example, by rotating the shaving cap relative to the container with sufficient force to overcome shearing resistance of the solidified gel. The cosmetic kit is particularly useful for hygienically cleansing the skin.

20 Claims, 1 Drawing Sheet

(56) References Cited

U.S. PATENT DOCUMENTS

| | | | |
|---|---|---|---|
| 2017/0189279 | A1 | 7/2017 | Lu et al. |
| 2021/0128420 | A1 | 5/2021 | Stebbins et al. |
| 2022/0062150 | A1 | 3/2022 | Liu et al. |
| 2022/0096344 | A1 | 3/2022 | Chiou |
| 2022/0096345 | A1 | 3/2022 | Chiou et al. |
| 2022/0202671 | A1 | 6/2022 | Stebbins et al. |
| 2022/0211599 | A1 | 7/2022 | Stebbins et al. |
| 2023/0108443 | A1 | 4/2023 | Yang et al. |

OTHER PUBLICATIONS

Database GNPD [Online] MINTEL; anonymous: "Botanical Cleansing Gel", 2021 XP093243322.
Database GNPD [Online] MINTEL; anonymous: "Glow Smoothie Jelly Cleanser", 2019 XP093243323.
Database GNPD [Online] MINTEL; anonymous: "The 3 in 1 Makeup Removing Marine Jelly", 2021 XP093243324.
Database GNPD [Online] MINTEL; anonymous: "Detox Cleansing Gel", 2023 XP093243333.

* cited by examiner

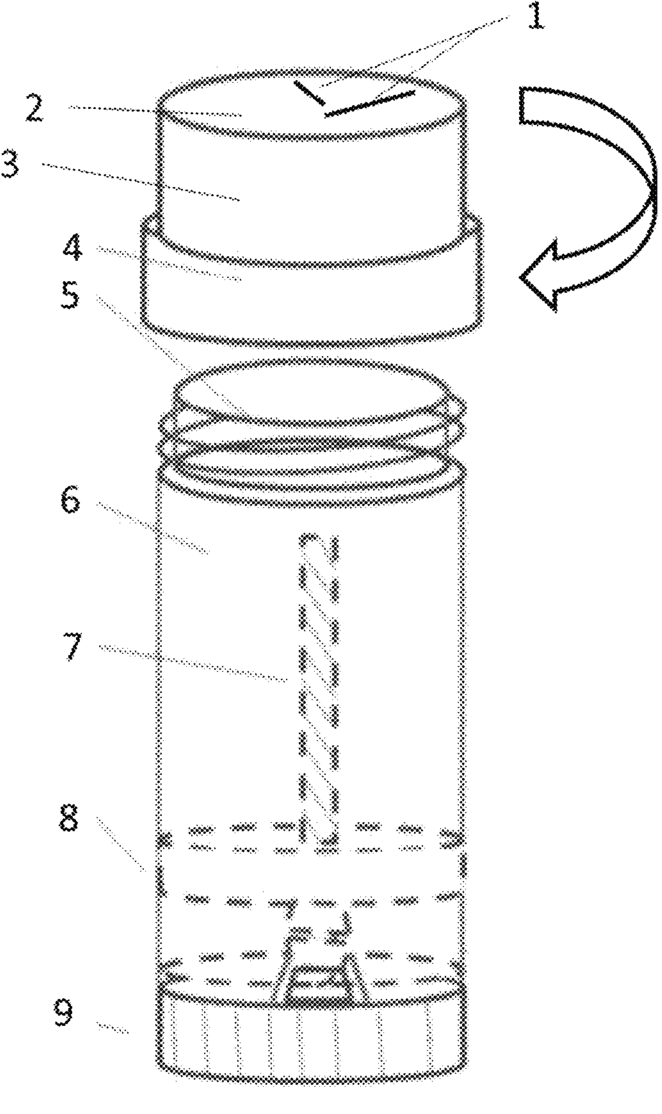
1
2
3
4
5
6
7
8
9

COSMETIC KIT WITH A CLEANSING STICK, DISPENSING CONTAINER, AND CUTTING DEVICE

FIELD OF THE DISCLOSURE

The present disclosure relates to a cosmetic kit comprising a container of a solidified gel and a shaving device for shaving away at least part of an exposed surface of the solidified gel.

BACKGROUND

Cosmetic and personal care products are stored and sold in containers that provide flexibility and convenience to consumers. Many cosmetic and personal care products are sold in containers or kits that include tools for easily dispensing and using the products. For example, eye liner products are packaged in bottles with lids that include an applicator brush, hair coloring products that include tools for accurately measuring, mixing, and applying the coloring composition to hair, and hair sprays are contained bottles that include pump or aerosol spraying devices. Consumers enjoy the convenience of these easy-to-use products.

Products for cleansing and caring for the skin are numerous, as individuals seek to improve the appearance of the skin, especially the skin of the face. Many products are available for application to the face including areas around the eyes. Examples include foundations, eye shadows, mascaras, eye liners, lipsticks and lip glosses, cleansers, toners, etc. Makeup temporarily improves the appearance and texture of the skin but the improvements are no permanent. Over time, the makeup eventually fades or wipes away from the skin. Makeup products are regularly removed or cleansed from the skin, usually daily, to maintain overall skin health. Failure to regularly remove makeup and cleanse the skin can lead to clogged pores, skin aging, breakdown of the skin barrier, inflammation, and flare-ups of underlying skin conditions like acne or rosacea.

Makeup removing products and cleansers are typically used for removing makeup from the skin. These products can be used on all parts of the face, including areas around the eyes. Makeup used around the eyes is usually very durable and is not easily removed. Durable makeup products are used to ensure the makeup is not easily removed, for example, when coming into contact with moisture from the eyes. Facial muscles around the eyes are in continuous movement to provide facial expression. Makeup applied around the eyes should be resistant to continuous movement without running, flaking, or clumping.

The eyes and the skin around the eyes are particularly sensitive. Therefore, certain makeup-removal and cleansing products have been designed specifically to remove makeup around the eyes. These products, however, continue to suffer from drawbacks. They often do not quickly and easily remove the makeup with a single application. Multiple applications of the makeup removing product or cleanser is needed to completely remove the makeup and cleanse the skin. Excessive scrubbing, rubbing, or tugging can irritate and even damage the skin.

There is a need for cosmetic cleansing compositions including makeup removing products that are particularly effective and are also easy to use without damaging or irritating the skin and eyes. It is important for cleansing products to cleanse the skin without causing irritation and without inadvertently contaminating the skin with germs that are ubiquitous throughout the environment. Therefore, skin care and cleansing products that easily dispense and deliver their content in a sanitary fashion are desirable.

BRIEF DESCRIPTION OF THE DRAWINGS

Implementation of the present technology is described, by way of example only, with reference to the attached FIGURE, wherein:

The FIGURE shows an example of a cosmetic kit with a container and a shaving cap.

The various aspects of the disclosure are not limited to the results, arrangements, and representations shown in the drawings.

SUMMARY OF THE DISCLOSURE

The present disclosure is drawn to a cosmetic kit comprising a container and a shaving cap. The container includes an interior chamber housing a solidified gel of a micellar solution and a dispensing opening that exposes an outer surface of the solidified gel. The exposed surface of the solidified gel is applied to skin, for example, to cleanse the skin. The shaving cap is useful for shaving at least a portion of the exposed surface of the solidified gel away from a mass of the solidified gel within the container. The exposed surface of the solidified gel may become contaminated due to contact with the atmosphere and contaminants on the skin. In such situations, the shaving cap is useful for "shaving" away the exposed surface of the solidified gel that may include contaminants, leaving behind a fresh and clean layer of the solidified gel for subsequent use. Thus, the cosmetic kit is particularly useful for hygienically treating and cleansing the skin.

The shaving cap comprises a substantially planer surface and one or more openings or slits through the planar surface having shaving edges that contact the exposed surface of the solidified gel. The shaving edges slice away at least a portion of the exposed surface when forced across the surface. For example, the shaving cap can be rotated relative to a mass of the solidified gel in the container with sufficient force to overcome shearing resistance of the solidified gel, thereby "shaving away" the portion of the mass of solidified gel.

The solidified gel is formed from a micellar solution and has a hardness of at least 2 N at 25° C. The solidified gel is preferably translucent or transparent. It is particularly effective for cleansing, hydrating, and nourishing the skin, including the skin of the face. The inventors discovered that amongst thickening agents, in particular, amongst polysaccharide thickening agents, gellan gum is surprisingly effective for generating a solidified gel of a micellar solution that is transparent, sufficient hard, and compatible with other ingredients that facilitate cleansing. The solidified gel has a pleasant texture that is not sticky. It glides easily over the skin while depositing a pleasant layer onto the skin. The deposited layer penetrates, dislodges, and dissolves contaminants (e.g., unwanted oils, sebum, makeup, and build-up) that can be subsequently wiped away or simply rinsed from the skin.

The cosmetic kit comprises a container housing a solidified gel of a micellar solution and a shaving cap, which can be removably engaged with the solidified gel or container. In particular, the cosmetic kit includes:

(i) a container with an interior chamber containing a solidified gel of a micellar solution and a dispensing opening that exposes an outer surface of the solidified gel, wherein the solidified gel comprises:

(a) about 1.2 wt. % or more of gellan gum;

(b) about 1 to about 10 wt. % of one or more polyols having from 2 to 10 carbon atoms;

(c) about 1 to about 10 wt. % of one or more surfactants; and (d) about 80 to about 95 wt. % of water;

wherein the solidified gel is transparent, has a hardness of at least 2 N at 25° C., and all weight percentages are based on a total weight of the solidified gel; and (ii) a shaving cap comprising a planar surface and one or more openings through the planar surface, and one or more shaving edges along the one or more openings, for shaving at least part of an exposed surface of the solidified gel extending through the dispensing opening of the container.

The shaving cap may be removably engaged with the container and/or with the exposed surface of the solidified gel. For example, the shaving cap preferably fits over the exposed surface of the solidified gel so that the one or more shaving edges can shave at least part of the exposed surface of the solidified gel, for example, when the shaving cap is rotated relative to the solidified gel. The shaving edges may be simply a beveled edge or may include a blade extending away from the planar surface. The beveled edge or blade extends away from the planar surface toward the exposed surface of the solidified gel when the shaving cap is engaged with the solidified gel and used to remove part of the exposed surface of the solidified gel. The shaving cap may be unified with a cover cap, which is used to close the container housing the solidified gel or may be a separate and distinct element. For example, the shaving cap may be sized such that it can stack inside or outside of the cover cap.

The container may be any suitable size and shape. Nonetheless, a convenient and preferable container may be cylindrical (a tube), wherein a bottom end of the cylinder or tube is closed and a top end of the cylinder or tube forms a dispensing opening. The container may also, optionally, include a supply mechanism, for example, within the interior chamber for advancing the solidified gel toward the dispensing opening. Thus, as the exposed outer surface of the solidified gel is used or shaved away, a mass of solidified gel inside the container can be continuously advanced toward and/or through the dispensing opening. The supply mechanism may optionally include a twist-up advance mechanism. This allows the consumer to manually control the advancement of the solidified gel by rotating a wheel. The container can be similar to chapstick containers that expel a chapstick through an opening or like a deodorant container that the advanced the solid deodorant stick upward through an opening when a rotating wheel is manually turned.

As noted above, the solidified gel is formed from a micellar solution and is typically transparent or translucent. A micellar solution comprising the gellan gum dissolved in water, and combined with the polyols, surfactants, and other ingredients of the solidified gel are combined into a micellar solution. The micellar solution is heated to a sufficient temperate for a sufficient amount of time to ensure the micellar solutions transforms into a solidified gel having a hardness of about 2 N (or about 200 gram-force) at 25° C.

Nonlimiting examples of polyols having from 2 to 10 carbon atoms include ethylene glycol, propylene glycol, butylene glycol, hexylene glycol, pentylene glycol, 1,3-propanediol, diethylene glycol, dipropylene glycol, caprylyl glycol, glycerin, or mixtures thereof. In various embodiments, the solidified gel includes glycerin and optionally, one or more additional polyols having from 2 to 10 carbon atoms, for example, selected from ethylene glycol, propylene glycol, butylene glycol, hexylene glycol, pentylene glycol, 1,3-propanediol, diethylene glycol, dipropylene glycol, caprylyl glycol, or mixtures there.

The solidified gel may include one or more surfactants, for example, surfactants selected from amphoteric surfactants, nonionic surfactants, anionic surfactants, cationic surfactants, or mixtures thereof. In a preferred embodiment, the solidified gel includes a plurality of surfactants (i.e., two or more surfactants). The plurality of surfactants may include one or more amphoteric surfactants, one or more nonionic surfactants, and optionally, one or more anionic surfactants.

Nonlimiting examples of amphoteric surfactants include alkyl amphoproprionates, betaines, alkyl sultaines, alkyl amphoacetates, or mixtures thereof. In a preferred embodiment, at least one of the one or more amphoteric surfactants is an alkyl amphoacetate, for example, selected from disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylampho-dipropionate, disodium caprylomphodipropionate, lauroamphodipropionic acid, cocoamphodipropionic acid, or mixtures thereof.

Nonlimiting examples of nonionic surfactants include poloxamers; polysorbates; alkyl polyglucosides; alcohols, alpha-diols, alkylphenols or esters of fatty acids, being optionally ethoxylated, propoxylated, or glycerolated (polyglyceryl-2 isostearate); ethoxylated fatty esters; glyceryl esters of fatty acids; fatty alcohol ethoxylates; alkyl phenol ethoxylates; fatty acid alkoxylates; and mixtures thereof. In a preferred embodiment, the solidified gel includes at least one poloxamer.

The solidified gel may optionally include one or more miscellaneous ingredients. Nonlimiting examples of miscellaneous ingredients include preservatives, fragrances, essential oils, chelating agents, antioxidants, flavonoids, vitamins, botanical extracts, UV filtering agents, proteins, protein hydrolysates, protein isolates, fillers, composition colorants, or mixtures thereof.

The solidified gel typically includes a large proportion of water and little, if any fatty compounds. For example, the solidified gel preferably includes less than 2 wt. % of fatty compounds, more preferably less than 1.5 wt. %, and even more preferably less than 1 wt. % of fatty compounds.

The solidified gel typically has a hardness of about 2 N (~200 gram force) or greater at 25° C. Nonetheless, in certain embodiments, the hardness may be about 2 to about 15 N, about 2 to about 12 N, about 2 to about 10 N, about 2 to about 5 N, about 3 to about 20 N, about 3 to about 15 N, about 3 to about 12 N, about 3 to about 10 N, about 3 to about 5 Na, about 5 to about 20 N, about 5 to about 15 N, about 5 to about 12 N, about 5 to about 10 N at 25° C.

The solidified gel can be cast, cut, or formed into a desired shape. For example, in one embodiment, the solidified gel is cast into a container and therefore takes the shape of the container. In a preferred embodiment, the solidified gel is in the shape of a cylinder.

The solidified gel is particularly useful in methods for treating skin, including methods for cleansing the skin and methods for removing makeup from skin, in particular, the skin of the face and the skin around the eyes. Such methods include applying the solidified gel to the skin and subsequently wiping, rinsing, or washing the solidified gel from the skin. In methods for cleansing the skin, the solidified gel may be applied to skin in need of cleansing. In methods for removing makeup from the skin, the solidified gel is applied to skin upon which makeup exists or is adhered. After application of the solidified gel to the skin, the solidified gel can optionally be massaged or rubbed over the skin, for example, with an individual hands and fingers.

Methods for making or producing the solidified gel are also disclosed. The solidified gel is manufactured by combining ingredients of the solidified gel and heating the composition to potentiate hardening of the composition into a solidified gel. Typically, the gellan gum is dissolved in water and additional ingredients are added to form a micellar solution. The micellar solution is heated to a temperature of about 70° C. for at least 5 minutes. Upon cooling to room temperature, the composition hardens into the solidified gel.

DETAILED DESCRIPTION OF THE DISCLOSURE

The cosmetic kit of the instant disclosure is particularly useful for cleansing, hydrating, and nourishing the skin. The cosmetic kit comprises a container housing a solidified gel of a micellar solution and a shaving cap, which can be removably engaged with the solidified gel or container. The cosmetic kit is easy to use, surprisingly effective, and aesthetically pleasing. Typically, the solidified gel is transparent and spreads effortlessly along the skin, leaving behind a cleansing layer of composition. The cleansing layer of the composition penetrates, dissolves, and lifts unwanted substances such as oils, sebum, and makeup from the skin, while simultaneously hydrating and softening the skin. The cosmetic kit is particularly well-suited and useful for removing makeup from the face, especially the delicate areas around the eyes. The solidified gel is gentle yet effectively and quickly removes makeup without causing irritation or damage to the skin, for example, irritation or damage caused by harsh detersive surfactants or excess scrubbing.

The cosmetic kit includes a container housing a solidified gel of a micellar solution and a shaving cap, which can be removably engaged with the solidified gel or container. For example, the cosmetic kit typically includes:

(i) a container with an interior chamber containing a solidified gel of a micellar solution and a dispensing opening that exposes an outer surface of the solidified gel, wherein the solidified gel comprises:
 (a) about 1.2 wt. % or more of gellan gum;
 (b) about 1 to about 10 wt. % of one or more polyols having from 2 to 10 carbon atoms;
 (c) about 1 to about 10 wt. % of one or more surfactants; and
 (d) about 80 to about 95 wt. % of water;
 wherein the solidified gel is transparent,
 has a hardness of at least 2 N at 25° C., and
 all weight percentages are based on a total weight of the solidified gel; and
(ii) a shaving cap comprising a planar surface and one or more openings through the planar surface, and one or more shaving edges along the one or more openings, for shaving at least part of an exposed surface of the solidified gel extending through the dispensing opening of the container.

The shaving cap may be removably engaged with the container or with the exposed surface of the solidified gel. For example, the shaving cap may fit over the exposed surface of the solidified gel so that the one or more shaving edges can shave at least part of the exposed surface of the solidified gel, for example, when the shaving cap is rotated relative to the solidified gel with sufficient force to overcome shearing resistance of the solidified gel. The shaving edges may optionally include a beveled edge or a blade extending away from the planar surface. The beveled edge or blade typically extend away from the planar surface toward the exposed surface of the solidified gel when the shaving cap is engaged with the solidified gel and used to remove part of the exposed surface of the solidified gel.

The term "micellar" as used throughout the disclosure is used in accordance with its ordinary and customary meaning. Along these lines, a micellar composition is a composition containing a dispersion of micelles, which are typically aggregated amphiphiles in equilibrium with free, unaggregated amphiphiles. Micellar compositions form when the concentration of amphiphile exceeds the critical micellar concentration (CMC) or critical aggregation concentration (CAC).

The solidified gel is not an emulsion or dispersion is homogenous and transparent or translucent, preferably transparent.

The solidified gel can include additional ingredients, for example, one or more miscellaneous ingredients. Nonlimiting examples of miscellaneous ingredients include preservatives, fragrances, essential oils, chelating agents, antioxidants, flavonoids, vitamins, botanical extracts, UV filtering agents, proteins, protein hydrolysates, protein isolates, fillers (e.g., silica, talc, other particulates, etc.), composition colorants, or mixtures thereof.

The solidified gel typically includes a large proportion of water and little, if any fatty compounds. For example, the solidified gel preferably includes less than 2 wt. % of fatty compounds, more preferably less than 1.5 wt. %, and even more preferably less than 1 wt. % of fatty compounds.

The hardness of the solidified gel will vary but is typically at least 2 N (at least 200 gram-force). In further embodiments, the hardness of the solidified gel is about 2 to about 15 N, about 2 to about 12 N, about 2 to about 10 N, about 2 to about 5 N, about 3 to about 20 N, about 3 to about 15 N, about 3 to about 12 N, about 3 to about 10 N, about 3 to about 5 N, about 5 to about 20 N, about 5 to about 15 N, about 5 to about 12 N, about 5 to about 10 N at 25° C. The hardness may also be from about 200 to about 1,500 gram-force, about 200 to about 1,200 gram-force, about 200 to about 1,000 gram-force, about 300 to about 1,500 gram-force, about 300 to about 1,200 gram-force, about 300 to about 1,000 gram-force, about 400 to about 1,500 gram-force, about 400 to about 1,200 gram-force, about 400 to about 1,000 gram-force, about 500 to about 1,500 gram-force, about 500 to about 1,200 gram-force, about 500 to about 1,000 gram-force at 25° C.

The solidified gel can be cast, cut, or formed into a desired shape. For example, in one embodiment, the solidified gel is in the form of a stick or bar. The stick or bar may be packaged in a container that allows a user to expel a portion of the stick or bar, as desired, from the container, for example, containers similar to containers used to package and deliver solid deodorant sticks or bars. The container may optionally include a supply mechanism, for example, within the interior chamber for advancing the solidified gel toward the dispensing opening. Thus, as the outer surface of the solidified gel is used or shaved away, a mass of solidified gel can be continuously advanced toward, and optionally advanced through, the dispensing opening. Furthermore, the supply mechanism may comprise a twist-up advance mechanism. This allows the consumer to manually control the advancement of the solidified gel by rotating the twist-up mechanism. For example, the advance mechanism may include an elevator, an elevator screw threadably engaging the elevator, and a rotatable hand-wheel for rotating the elevator screw.

(a) Gellan Gum

Gellan gum is a water-soluble anionic polysaccharide produced by the bacterium *Sphingomonas elodea*. Applicant found that gellan gum is particularly well-suited for solidifying a micellar solution of the instant case. When solubilized in water and heated to a temperature of about 70° C. or higher, the gellan gum causes a gelling effect and solidification of the solidified gel. The solidified gel has a pleasant (smooth) consistency, is transparent or translucent, and can be cast or cut into a desired size and shape.

The total amount of gellan gum in the solidified gel will vary but is typically about 1.2 wt. % or more, based on the total weight of the solidified gel. In further embodiments, the solidified gel includes about 1.3 wt. % or more, about 1.4 wt. % or more, about 1.5 wt. % or more of gellan gum. For example, the solidified gel may include from about 1.2 to about 5 wt. %, about 1.2 to about 4 wt. %, about 1.2 to about 3 wt. %, about 1.2 to about 2 wt. %, about 1.3 to about 5 wt. %, about 1.3 to about 4 wt. %, about 1.3 to about 3 wt. %, about 1.3 to about 2 wt. %, about 1.43 to about 5 wt. %, about 1.4 to about 4 wt. %, about 1.4 to about 3 wt. %, about 1.4 to about 2 wt. %, about 1.5 to about 5 wt. %, about 1.5 to about 4 wt. %, about 1.5 to about 3 wt. %, about 1.5 to about 2 wt. % of gellan gum, based on the total weight of the solidified gel.

(b) Polyols

The solidified gel typically includes one or more polyols having from 2 to 10 carbon atoms. Preferably the polyols also have two or three hydroxyl groups. For example, the polyols can be selected from glycols and glycerol. Nonlimiting examples of polyols having from 2 to 10 carbon atoms include ethylene glycol, propylene glycol, butylene glycol, hexylene glycol, pentylene glycol, 1,3-propanediol, diethylene glycol, dipropylene glycol, caprylyl glycol, glycerin, and combinations thereof. In a preferred embodiment, the solidified gel includes glycerin and one or more additional polyols having from 2 to 10 carbon atoms. In a further embodiment, the solidified gel includes glycerin and one or more glycol selected from ethylene glycol, propylene glycol, butylene glycol, hexylene glycol, pentylene glycol, diethylene glycol, dipropylene glycol, or combinations thereof.

The total amount of the one or more polyols having from 2 to 10 carbon atoms in the solidified gel will vary but is typically about 1 to about 20 wt. %, based on the total weight of the solidified gel. In further embodiments, the solidified gel includes about 1 to about 15 wt. %, about 1 to about 12 wt. %, about 1 to about 10 wt. %, about 1 to about 8 wt. %, about 1 to about 5 wt. %, about 2 to about 20 wt. %, about 2 to about 15 wt. %, about 2 to about 12 wt. %, about 2 to about 10 wt. %, about 2 to about 8 wt. %, or about 2 to about 5 wt. %, based on the total weight of the solidified gel. Preferably, the solidified gel includes about 1 to about 15 wt. %, more preferably about 1 to about 10 wt. %, and even more preferably, about 2 to about 8 wt. % of one or more polyols.

(c) Surfactants

The solidified gel typically includes one or more surfactants. The term "surfactants" is intended to also cover "emulsifiers." Surfactants include nonionic surfactants, amphoteric surfactants, anionic surfactants, and cationic surfactants.

The total amount of the one or more surfactants in the solidified gel will vary but is typically about 0.1 to about 20 wt. %, based on the total weight of the solidified gel. In further embodiments, the solidified gel includes about 0.1 to about 15 wt. %, about 0.1 to about 10 wt. %, 0.1 to about 8 wt. %, about 0.1 to about 5 wt. %, about 0.5 to about 20 wt. %, about 0.5 to about 15 wt. %, about 0.5 to about 10 wt. %, about 0.5 to about 8 wt. %, about 0.5 to about 5 wt. %, about 1 to about 10 wt. %, about 1 to about 8 wt. %, about 1 to about 5 wt. %, about 2 to about 20 wt. %, about 2 to about 15 wt. %, about 2 to about 10 wt. %, about 2 to about 8 wt. %, about 2 to about 5 wt. %, based on the total weight of the solidified gel.

(c)(i) Amphoteric Surfactants

The solidified gel preferably includes one or more amphoteric surfactants. Nonlimiting examples of amphoteric surfactants include alkyl amphoproprionates, betaines, alkyl sultaines, alkyl amphoacetates, and combinations thereof.

Nonlimiting examples of alkyl amphopropionates include cocoamphopropionate, cornamphopropionate, caprylamphopropionate, cornamphopropionate, caproamphopropionate, oleoamphopropionate, isostearoamphopropionate, stearoamphopropionate, lauroamphopropionate, salts thereof, and a combination thereof.

Nonlimiting examples of betaines include coco betaine, cocamidopropyl betaine, lauryl betaine, laurylhydroxy sulfobetaine, lauryldimethyl betaine, cocamidopropyl hydroxysultaine, behenyl betaine, capryl/capramidopropyl betaine, lauryl hydroxysultaine, stearyl betaine, and combinations thereof.

Nonlimiting examples of alkyl sultaines include cocamidopropyl hydroxysultaine and lauryl hydroxysultaine.

Nonlimiting examples of an alkyl amphoacetates include disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylampho-dipropionate, disodium caprylomphodipropionate, lauroamphodipropionic acid, cocoamphodipropionic acid, or mixtures thereof. In a preferred embodiment, the solidified gel includes one or more alkyl amphoacetates. In a preferred embodiment, the alkyl amphoacetate is selected from sodium lauroamphoacetate, disodium cocoamphodiacetate, or a combination thereof.

(c)(ii) Nonionic Surfactants

The solidified gel preferably includes one or more nonionic surfactants. Nonlimiting examples of nonionic surfactants include poloxamer surfactants; polysorbates; alkyl polyglucosides; alcohols, alpha-diols, alkylphenols and esters of fatty acids, being ethoxylated, propoxylated or glycerolated (polyglyceryl-2 isostearate); ethoxylated fatty esters; glyceryl esters of fatty acids; fatty alcohol ethoxylates; alkyl phenol ethoxylates; fatty acid alkoxylates; and mixtures thereof.

In a preferred embodiment, the solidified gel includes one or more poloxamer surfactants.

Poloxamers are nonionic triblock copolymers composed of a central hydrophobic chain of polyoxypropylene (poly (propylene oxide)) flanked by two hydrophilic chains of polyoxyethylene (poly(ethylene oxide)). The term poloxamer surfactant refers to a polyethylene oxide-polypropylene oxide-polyethylene oxide (PEG-PPG-PEG) nonionic triblock copolymer. Poloxamer surfactants include nonionic triblock copolymers such as polyoxyethylene oxide-polyoxypropylene oxide-polyoxyethylene oxide (PEO-PPO-PEO) characterized by a central hydrophobic chain of polyoxypropylene (poly(propylene oxide)) flanked by two hydrophilic chains of polyoxyethylene (poly(ethylene oxide)). Exemplary nonionic triblock copolymers may comprise a structure according to Formula (A):

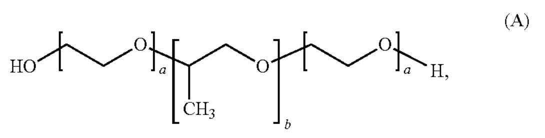

wherein each a is independently an integer in the range of 2-130, and b is an integer in the range of 15-67. In some embodiments, a is in the range of 50-100 and b is in the range of 20-40. In some embodiments, a is in the range of 70-90 and b is in the range of 25-30. Nonlimiting examples of poloxamers include poloxamer 188, also known as Pluronic® F-68, or KOLLIPHOR® P188, e.g., having a=80 and b=27. Other poloxamers include poloxamer 338, also known as Synperonic® PE/F108, poloxamer 407, also known as Synperonic® PE/F127, poloxamer 331, also known as Synperonic® PE/L101.

The term "PLURONIC® F68," "Pluronic F-68", or "PF-68", also known as poloxamer 188, refers to poly(ethylene glycol)-block-poly(propylene glycol)-block poly(ethylene glycol) copolymer with an average molecular weight, avg. Mn, of 8350-8400. The term "PLURONIC® F127" also known as poloxamer 407 refers to a triblock copolymer consisting of a central hydrophobic block of polypropylene glycol flanked by two hydrophilic blocks of polyethylene glycol (PEG). The approximate lengths of the two PEG blocks is 101 repeat units, while the approximate length of the propylene glycol block is 56 repeat units. This is also known by the Croda trade name Synperonic® PE/F 127. The term "PLURONIC® F108" refers to poly(ethylene glycol)-block-poly(propylene glycol)-block poly(ethylene glycol). The term "PLURONIC® P103" refers to poly(ethylene glycol)-block-poly(propylene glycol)-block poly(ethylene glycol). The term "PLURONIC® P104" refers to poly (ethylene glycol)-block-poly(propylene glycol)-block poly (ethylene glycol). The term "PLURONIC® P123" refers to poly(ethylene glycol)-block-poly(propylene glycol)-block poly(ethylene glycol).

Nonlimiting examples of poloxamers include Nonlimiting examples of poloxamers include poloxamer-101, poloxamer-105, poloxamer-105 benzoate, poloxamer-108, poloxamer-122, poloxamer-123, poloxamer-124, poloxamer-181, poloxamer-182, poloxamer-182 dibenzoate, poloxamer-183, poloxamer-184, poloxamer-185, poloxamer-188, poloxamer-212, poloxamer-215, poloxamer-217, poloxamer-231, poloxamer-234, poloxamer-235, poloxamer-237, poloxamer-238, poloxamer-282, poloxamer-284, poloxamer-288, poloxamer-331, poloxamer-333, poloxamer-334, poloxamer-335, poloxamer-338, poloxamer-401, poloxamer-402, poloxamer-403, and poloxamer-407.

The lengths of the polymer blocks can be customized and therefore, many different poloxamers exist that have slightly different properties. Poloxamer copolymers are commonly named with the letter "P" (for poloxamer) followed by three digits, the first two digits×100 give the approximate molecular mass of the polyoxypropylene core, and the last digit×10 gives the percentage polyoxyethylene content (e.g., P407=Poloxamer with a polyoxypropylene molecular mass of 4,000 g/mol and a 70% polyoxyethylene content). For the Pluronic® and Synperonic® poloxamer tradenames, coding of these copolymers starts with a letter to define its physical form at room temperature (L=liquid, P=paste, F=flake (solid)) followed by two or three digits. The first digit (two digits in a three-digit number) in the numerical designation, multiplied by 300, indicates the approximate molecular weight of the hydrophobic chain; and the last digit×10 gives the percentage polyoxyethylene content (e.g., F-68 indicates a polyoxypropylene molecular mass of 1,800 g/mol and a 80% polyoxyethylene content). An exemplary poloxamer is Pluronic F-68®. PF-68 is a nonionic triblock copolymer polyoxyethylene oxide-polyoxypropylene oxide-polyoxyethylene oxide (PEO-PPO-PEO). Commercially available poloxamers include PLURONIC® surfactants such as PLURONIC® F68, F77, F87, F98, F108, F127, P103, P104, P105, and P123.

The total amount of the one or more poloxamer surfactants in the solidified gel, if present, will vary but is typically about 0.1 to about 10 wt. %, based on the total weight of the solidified gel. In further embodiments, the solidified gel includes about 0.1 to about 8 wt. %, about 0.1 to about 5 wt. %, about 0.1 to about 3 wt. %, about 0.5 to about 10 wt. %, about 0.5 to about 5 wt. %, about 0.5 to about 3 wt. %, about 1 to about 10 wt. %, about 1 to about 8 wt. %, about 1 to about 5 wt. %, or about 1 to about 3 wt. % of one or more poloxamer surfactants, based on the total weight of the solidified gel. Preferably, the solidified gel includes about 0.1 to about 10 wt. %, preferably about 0.5 to about 8 wt. %, and even more preferably about 0.5 to about 5 wt. % of one or more poloxamer surfactants, based on the total weight of the solidified gel.

Nonionic surfactants also include those of the alkyl(poly) glycoside type, represented especially by the following general formula: $R_1O—(R_2O)_t-(G)_v$ in which: $R_1$ represents a linear or branched alkyl or alkenyl substituent comprising 6 to 24 carbon atoms and especially 8 to 18 carbon atoms, or an alkylphenyl substituent whose linear or branched alkyl substituent comprises 6 to 24 carbon atoms and especially 8 to 18 carbon atoms; $R_2$ represents an alkylene substituent comprising 2 to 4 carbon atoms; G represents a sugar unit comprising 5 to 6 carbon atoms; t denotes a value ranging from 0 to 10 and preferably 0 to 4; and v denotes a value ranging from 1 to 15 and preferably 1 to 4. Preferably, the alkyl(poly)glycoside surfactants are compounds of the formula described above in which: $R_1$ denotes a linear or branched, saturated or unsaturated alkyl substituent comprising from 8 to 18 carbon atoms; $R_2$ represents an alkylene substituent comprising 2 to 4 carbon atoms; t denotes a value ranging from 0 to 3 and preferably equal to 0; and G denotes glucose, fructose or galactose, preferably glucose; the degree of polymerization, i.e. the value of v, possibly ranging from 1 to 15 and preferably from 1 to 4; the mean degree of polymerization more particularly being between 1 and 2. The glucoside bonds between the sugar units are generally of 1-6 or 1-4 type and preferably of 1-4 type. In particular, the alkyl(poly)glycoside surfactant may be an alkyl(poly) glucoside surfactant $C_8/C_{16}$ alkyl(poly) glucosides 1,4, and in particular decyl glucosides and caprylyl/capryl glucosides.

Nonionic surfactants include polyoxyethylenated C8-C30 fatty acid esters (preferably C12-C18) of sorbitan, polyethoxylated C8-C30 (preferably C12-18) fatty alcohols, polyglycerolated C8-C30 (preferably C12-C18) fatty acid esters, polyoxyethylenated compounds having preferably from 2 to 30 moles of ethylene oxide, polyglycerolated compounds having preferably from 2 to 16 moles of glycerol; and mixtures thereof. The polyoxyethylenated C8-C30 fatty alcohols may be chosen from C12-C18 fatty alcohols, in particular polyoxyethylenated lauryl alcohol, cetyl alcohol, myristyl alcohol, and stearyl alcohol having from 2 to 30 mol of ethylene oxide, such as: cetyl alcohol polyoxyethylenated with 2 EO (Ceteth-2) (HLB 5.3) cetyl alcohol polyoxyethylenated with 6 EO (Ceteth-6) (HLB 11.1) cetyl alcohol polyoxyethylenated with 10 EO (Ceteth-10) (HLB 12.9) cetyl alcohol polyoxyethylenated with 20 EO (Ceteth-20) (HLB 15.7) cetyl alcohol polyoxyethylenated with 24 EO (Ceteth-24) (HLB 16.3) lauryl alcohol polyoxyethylenated with 2 EO (laureth-2) (HLB 6.1) lauryl alcohol polyoxyethylenated with 3 EO (laureth-3) (HLB 8) lauryl alcohol polyoxyethylenated with 4 EO (laureth-4) (HLB 9.4) lauryl alcohol polyoxyethylenated with 7 EO (laureth-7) (HLB 12.3) lauryl alcohol polyoxyethylenated with 9 EO (laureth-9) (HLB 13.6) lauryl alcohol polyoxyethylenated with 10 EO (laureth-10) (HLB 13.9) lauryl alcohol polyoxyethylenated with 12 EO (laureth-12) (HLB 14.6) lauryl alcohol polyoxyethylenated with 21 EO (laureth-21) (HLB 15.5) lauryl alcohol polyoxyethylenated with 23 EO (laureth-23) (HLB 16.3) stearyl alcohol polyoxyethylenated with 2 EO (Steareth-2) (HLB 4.9) stearyl alcohol polyoxyethylenated with 10 EO (Steareth-10) (HLB 12.4) stearyl alcohol polyoxyethylenated with 20 EO (Steareth-20) (HLB 15.2) stearyl alcohol polyoxyethylenated with 21 EO (Steareth-21) (HLB 15.5).

The polyoxyethylenated C8-C30 fatty acid esters (preferably C12-C18) of sorbitan may be chosen from polyoxyethylenated esters of C12-C18 fatty acids, in particular lauric, myristic, cetylic or stearic acids, of sorbitan especially containing from 2 to 30 mol of ethylene oxide, such as: polyoxyethylenated sorbitan monolaurate (4 EO) (Polysorbate-21) (HLB 13.3) polyoxyethylenated sorbitan monolaurate (20 EO) (Polysorbate-20) (HLB 16.7) polyoxyethylenated sorbitan monopalmitate (20 EO) (Polysorbate-40) (HLB 15.6) polyoxyethylenated sorbitan monostearate (20 EO) (Polysorbate-60) (HLB 14.9) polyoxyethylenated sorbitan monostearate (4 EO) (Polysorbate-61) (HLB 9.6) polyoxyethylenated sorbitan monooleate (20 EO) (Polysorbate-80) (HLB 15). In a preferred embodiment, the solidified gels include one or more nonionic surfactants chosen from polyoxyethylenated C8-C30 fatty acid esters (preferably C12-C18) of sorbitan, preferably polyoxyethylenated esters of C12-C18 fatty acids.

The polyglycerolated C8-C30 fatty acid esters, which are particularly preferred, may be chosen from polyglycerolated esters of C12-C18 fatty acids, in particular lauric, myristic, palmitic, stearic or isostearic acid, having from 2 to 16 mol of glycerol, such as: polyglyceryl-2 laurate, polyglyceryl-3 laurate, polyglyceryl-4 laurate, polyglyceryl-5 laurate, polyglyceryl-6 laurate, polyglyceryl-10 laurate; polyglyceryl-2 myristate, polyglyceryl-3 myristate, polyglyceryl-4 myristate, polyglyceryl-5 myristate, polyglyceryl-6 myristate, polyglyceryl-10 myristate; polyglyceryl-2 palmitate, polyglyceryl-3 palmitate, polyglyceryl-6 palmitate, polyglyceryl-10 palmitate; polyglyceryl-2 isostearate, polyglyceryl-3 isostearate, polyglyceryl-4 isostearate, polyglyceryl-5 isostearate, polyglyceryl-6 isostearate, polyglyceryl-10 isostearate; polyglyceryl-2 stearate, polyglyceryl-3 stearate, polyglyceryl-4 stearate, polyglyceryl-5 stearate, polyglyceryl-6 stearate, polyglyceryl-8 stearate, polyglyceryl-10 stearate, and mixtures thereof.

In some cases, the nonionic surfactant may be selected from esters of polyols with fatty acids with a saturated or unsaturated chain containing for example from 8 to 24 carbon atoms, preferably 12 to 22 carbon atoms, and alkoxylated derivatives thereof, preferably with a number of alkyleneoxide of from 10 to 200, and more preferably from 10 to 100, such as glyceryl esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; polyethylene glycol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sorbitol esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; sugar (sucrose, glucose, alkylglycose) esters of a $C_8$-$C_{24}$, preferably $C_{12}$-$C_{22}$, fatty acid or acids and alkoxylated derivatives thereof, preferably with a number of alkyleneoxide of from 10 to 200, and more preferably from 10 to 100; ethers of fatty alcohols; ethers of sugar and a $C_8$-$C_{24}$, preferably $C_{12}$-$C_{22}$, fatty alcohol or alcohols; and mixtures thereof.

Examples of ethoxylated fatty esters that may be mentioned include the adducts of ethylene oxide with esters of lauric acid, palmitic acid, stearic acid or behenic acid, and mixtures thereof, especially those containing from 9 to 100 oxyethylene groups, such as PEG-9 to PEG-50 laurate (as the CTFA names: PEG-9 laurate to PEG-50 laurate); PEG-9 to PEG-50 palmitate (as the CTFA names: PEG-9 palmitate to PEG-50 palmitate); PEG-9 to PEG-50 stearate (as the CTFA names: PEG-9 stearate to PEG-50 stearate); PEG-9 to PEG-50 palmitostearate; PEG-9 to PEG-50 behenate (as the CTFA names: PEG-9 behenate to PEG-50 behenate); polyethylene glycol 100 EO monostearate (CTFA name: PEG-100 stearate); and mixtures thereof.

As glyceryl esters of fatty acids mention is made of glyceryl stearate (glyceryl monostearate, distearate, and/or tristearate) (CTFA name: glyceryl stearate) or glyceryl ricinoleate and mixtures thereof. As glyceryl esters of C8-C24 alkoxylated fatty acids, polyethoxylated glyceryl stearate (glyceryl mono-, di- and/or tristearate) such as PEG-20 glyceryl stearate can for example be cited Nonlimiting examples of alkyl polyglucosides include lauryl glucoside, octyl glucoside, decyl glucoside, coca glucoside, sucrose laurate, caprylyl/capryl glucoside, and sodium lauryl glucose carboxylate, and mixtures thereof.

Suitable alkoxylated monoacid surfactants include, but are not limited to: butoxynol-5 carboxylic acid, butoxynol-19 carboxylic acid, capryleth-4 carboxylic acid, capryleth-6 carboxylic Acid, capryleth-9 carboxylic acid, ceteareth-25 carboxylic acid, coceth-7 carboxylic acid, C9-11 pareth-6 carboxylic acid, C11-15 pareth-7 carboxylic acid, C12-13 pareth-5 carboxylic acid, C12-13 pareth-8 carboxylic acid, C12-13 pareth-12 carboxylic acid, C12-15 pareth-7 carboxylic acid, C12-15 pareth-8 carboxylic acid, C14-15 pareth-8 carboxylic acid, deceth-7 carboxylic acid, laureth-3 carboxylic acid, laureth-4 carboxylic Acid, laureth-5 carboxylic acid, laureth-6 carboxylic acid, laureth-8 carboxylic acid, laureth-10 carboxylic acid, laureth-11 carboxylic acid, laureth-12 carboxylic acid, laureth-13 carboxylic acid, laureth-14 carboxylic acid, laureth-17 carboxylic acid, PPG-6-laureth-6 carboxylic acid, PPG-8-steareth-7 carboxylic acid, myreth-3 carboxylic acid, myreth-5 carboxylic acid, Nonoxynol-5 carboxylic acid, nonoxynol-8 carboxylic acid, Nonoxynol-10 carboxylic acid, octeth-3 carboxylic acid, octoxynol-20 carboxylic acid, oleth-3 carboxylic acid, oleth-6 carboxylic acid, oleth-10 carboxylic acid, PPG-3-deceth-2 carboxylic acid, capryleth-2 carboxylic acid, Ceteth-13 carboxylic acid, deceth-2 carboxylic acid, hexeth-4 carboxylic acid, isosteareth-6 carboxylic acid, isosteareth-11 carboxylic acid, trudeceth-3 carboxylic acid, trideceth-6 carboxylic acid, trideceth-8 carboxylic acid, trideceth-12 carboxylic acid, trideceth-3 carboxylic acid, trideceth-4 carboxylic acid, trideceth-7 carboxylic acid, trideceth-15 carboxylic acid, trideceth-19 carboxylic acid, undeceth-5 carboxylic acid and combinations thereof.

The total amount of the one or more nonionic surfactants in the solidified gel, if present, will vary but is typically about 0.1 to about 15 wt. %, based on the total weight of the solidified gel. In further embodiments, the solidified gel includes about 0.1 to about 12 wt. %, about 0.1 to about 10 wt. %, about 0.1 to about 8 wt. %, bout 0.1 to about 5 wt. %, about 0.1 to about 3 wt. %, about 0.5 to about 15 wt. %, about 0.5 to about 12 wt. %, about 0.5 to about 10 wt. %, about 0.5 to about 8 wt. %, about 0.5 to about 5 wt. %, about 0.5 to about 3 wt. %, about 1 to about 15 wt. %, about 1 to about 12 wt. %, about 1 to about 10 wt. %, about 1 to about 8 wt. %, about 1 to about 5 wt. %, or about 1 to about 3 wt. % of one or more nonionic surfactants, based on the total weight of the solidified gel.

(c)(iii) Anionic Surfactants

The solidified gel may include one or more anionic surfactants. Anionic surfactants have a negative charge on their hydrophilic end. The negative charge contributes to its ability to lift and suspend soils in micelles. Due to their effective cleansing properties, in certain embodiments, the solidified gel preferably includes one or more anionic surfactants. Nonlimiting examples of anionic surfactants include sulfates, acyl isethionates, acyl amino acids (such as acyl taurates, acyl glycinates, acyl glutamates, and acyl sarcosinates), alkyl sulfonates, alkyl sulfosuccinates, alkyl sulfoacetates, alkoxylated monoacids, salts thereof, and a combination thereof.

The total amount of anionic surfactants in the solidified gel, if present, will vary but is typically about 0.01 to about 15 wt. %, based on the total weight of the solidified gel. In further embodiments, the solidified gel includes about 0.01 to about 10 wt. %, about 0.01 to about 8 wt. %, about 0.01 to about 5 wt. %, about 0.1 to about 15 wt. %, about 0.1 to about 10 wt. %, about 0.1 to about 8 wt. %, about 0.1 to about 5 wt. %, about 0.5 to about 15 wt. %, about 0.5 to about 12 wt. %, about 0.5 to about 10 wt. %, about 0.5 to about 8 wt. %, about 0.5 to about 5 wt. %, about 1 to about 15 wt. %, about 1 to about 10 wt. %, about 1 to about 8 wt. %, about 1 to about 5 wt. %, about 2 to about 10 wt. %, about 2 to about 8 wt. %, or about 2 to about 5 wt. % of one or more anionic surfactants, based on the total weight of the solidified gel. Preferably, when included in the solidified gel, the one or more anionic surfactants are in an amount of about 0.1 to about 12 wt. %, preferably about 1 to about 10 wt. %, more preferably about 1 to about 8 wt. %, and even more preferably about 2 to about 5 wt. %, based on the total weight of the solidified gel.

(i) Sulfates

Sulfates (or "sulfate surfactants") have excellent cleansing and foaming properties. Therefore, in various embodiments, the solidified gel preferably includes one or more sulfates. In some cases, however, sulfate surfactants may be too harsh and therefore, the solidified gel is preferably free or essentially free from sulfates. Nonlimiting examples of sulfates include alkyl sulfates and alkyl ether sulfates. Useful alkyl sulfates include, but are not limited to, $C_{8-18}$ alky sulfates, more preferably $C_{12-18}$ alkyl sulfates, preferably in the form of a salt with a solubilizing cation such as sodium, potassium, ammonium or substituted ammonium. Nonlimiting examples include sodium lauryl sulfate (SLS), sodium dodecyl sulfate (SDS), or a combination thereof. Useful alkyl ether sulfates include, but are not limited to, those having the formula: $RO(CH_2CH_2O)_nSO_3M$; wherein R is an alkyl or alkenyl having from 8 to 18 (preferably 12 to 18) carbon atoms; n is a number having an average value of greater than at least 0.5, preferably between 1 and 3, more preferably between 2 and 3; and M is a solubilizing cation such as sodium, potassium, ammonium or substituted ammonium. An example is sodium lauryl ether sulfate (SLES).

The total amount of the one or more sulfates, if present, will vary but is typically about 0.01 to about 10 wt. %, based on the total weight of the solidified gel. In further embodiments, the solidified gel includes about 0.01 to about 8 wt. %, about 0.01 to about 5 wt. %, about 0.1 to about 10 wt. %, about 0.1 to about 8 wt. %, about 0.1 to about 5 wt. %, about 0.5 to about 10 wt. %, about 0.5 to about 8 wt. %, about 0.5 to about 5 wt. %, about 1 to about 10 wt. %, about 1 to about 8 wt. %, about 1 to about 5 wt. %, about 2 to about 10 wt. %, about 2 to about 8 wt. %, or about 2 to about 5 wt. % of one or more sulfates, based on the total weight of the solidified gel. Preferably, when included in the solidified gel, the one or more sulfates are in an amount of about 0.1 to about 12 wt. %, preferably about 1 to about 10 wt. %, more preferably about 1 to about 8 wt. %, and even more preferably about 2 to about 5 wt. %, based on the total weight of the solidified gel.

(ii) Acyl Amino Acids

The solidified gel may include one or more acyl amino acids. Nonlimiting examples include surfactants based on alanine, arginine, aspartic acid, glutamic acid, glycine, isoleucine, leucine, lysine, phenylalanine, serine, tyrosine, valine, sarcosine, threonine, and taurine. Common cations associated with acyl amino acids are sodium and potassium. Alternatively, the cation can be an organic salt such as triethanolamine (TEA) or a metal salt. Non-limiting examples of useful acyl amino acids include those of formula (I):

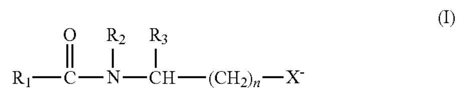

(I)

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$.

(ii-a) Acyl Sarcosinates

Nonlimiting examples of acyl sarcosinates include those of Formula (II) or salt thereof:

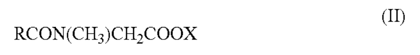

(II)

wherein R is C8 to C22 alkyl or alkenyl, X is hydrogen, alkali metal, ammonium, C1 to C6 alkylamine or amino alcohol.

More specific but nonlimiting examples of acyl sarcosinates include potassium lauroyl sarcosinate, potassium cocoyl sarcosinate, sodium cocoyl sarcosinate, sodium lauroyl sarcosinate, sodium myristoyl sarcosinate, sodium oleoyl sarcosinate, sodium palmitoyl sarcosinate, and ammonium lauroyl sarcosinate. In some instances, sodium lauroyl sarcosinate is preferred.

The total amount of the one or more acyl sarcosinates in the solidified gel, if present, will vary but is typically about 0.01 to about 10 wt. %, based on the total weight of the solidified gel. In further embodiments, the solidified gel includes about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, or about 0.5 to about 3 wt. % of one or more acyl sarcosinates, based on the total weight of the solidified gel.

(ii-b) Acyl Taurates

Non-limiting examples of acyl taurates include those of formula (III):

(III)

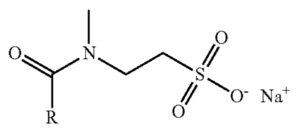

wherein R, $R^1$, $R^2$ and $R^3$ are each independently selected from H or an alkyl chain having 1-24 carbon atoms, or from 6-20 carbon atoms, or from 8 to 16 carbon atoms, said chain being saturated or unsaturated, linear, or branched, and X is $COO^-$ or $SO_3^-$. Non-limiting examples of acyl taurate salts include sodium cocoyl taurate and sodium methyl cocoyl taurate.

The total amount of the one or more acyl taurates in the solidified gel, if present, will vary but is typically about 0.01 to about 10 wt. %, based on the total weight of the solidified gel. In further embodiments, the solidified gel includes about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, or about 0.5 to about 3 wt. % of one or more acyl taurates, based on the total weight of the solidified gel.

(ii-c) Acyl Glycinates

Nonlimiting examples of useful acyl glycinates include those of formula (IV):

(IV)

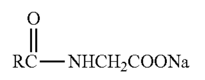

wherein R is an alkyl chain of 8 to 16 carbon atoms. Sodium is shown as the cation in the above formula (IV) but the cation may be an alkali metal ion such as sodium or potassium, ammonium ions, or alkanolammonium ions such as monoethanolammonium or triethanolammonium ions. Non-limiting examples of acyl glycinates include sodium cocoyl glycinate, sodium lauroyl glycinate, sodium myristoyl glycinate, potassium lauroyl glycinate, and potassium cocoyl glycinate, and in particular sodium cocoyl glycinate.

The total amount of the one or more acyl glycinates in the solidified gel, if present, will vary but is typically about 0.01 to about 10 wt. %, based on the total weight of the solidified gel. In further embodiments, the solidified gel includes about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, or about 0.5 to about 3 wt. % of one or more acyl glycinates, based on the total weight of the solidified gel.

(ii-d) Acyl Glutamates

Non-limiting examples of useful acyl glutamates include those of formula (V):

(V)

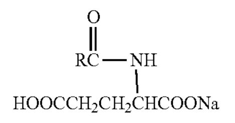

wherein R is an alkyl chain of 8 to 16 carbon atoms. Sodium is shown as the cation in the above formula (XI) but the cation may be an alkali metal ion such as sodium or potassium, ammonium ions, or alkanolammonium ions such as monoethanolammonium or triethanolammonium ions. Non-limiting examples of acyl glutamates include dipotassium capryloyl glutamate, dipotassium undecylenoyl glutamate, disodium capryloyl glutamate, disodium cocoyl glutamate, disodium lauroyl glutamate, disodium stearoyl glutamate, disodium undecylenoyl glutamate, potassium capryloyl glutamate, potassium cocoyl glutamate, potassium lauroyl glutamate, potassium myristoyl glutamate, potassium stearoyl glutamate, potassium undecylenoyl glutamate, sodium capryloyl glutamate, sodium cocoyl glutamate, sodium lauroyl glutamate, sodium myristoyl glutamate, sodium olivoyl glutamate, sodium palmitoyl glutamate, sodium stearoyl glutamate, sodium undecylenoyl glutamate, triethanolamine mono-cocoyl glutamate, triethanolamine lauroylglutamate, and disodium cocoyl glutamate. In some cases, sodium stearoyl glutamate is particularly preferred.

The total amount of the one or more acyl glutamate in the solidified gel, if present, will vary but is typically about 0.01 to about 10 wt. %, based on the total weight of the solidified gel. In further embodiments, the solidified gel includes about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, or about 0.5 to about 3 wt. % of one or more acyl glutamate, based on the total weight of the solidified gel.

(ii-e) Alkyl Sulfonates

Nonlimiting examples of alkyl sulfonates include alkyl aryl sulfonates, primary alkane disulfonates, alkene sulfonates, hydroxyalkane sulfonates, alkyl glyceryl ether sulfonates, alpha-olefinsulfonates, sulfonates of alkylphenolpolyglycol ethers, alkylbenzenesulfonates, phenylalkanesulfonates, alpha-olefinsulfonates, olefin sulfonates, alkene sulfonates, hydroxyalkanesulfonates and disulfonates, secondary alkanesulfonates, paraffin sulfonates, ester sulfonates, sulfonated fatty acid glycerol esters, and alpha-sulfo fatty acid methyl esters including methyl ester sulfonate.

In some instances, an alkyl sulfonate of formula (VI) is particularly useful.

(VI)

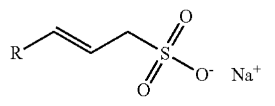

R is selected from H or alkyl chain that has 1-24 carbon atoms, preferably 6-24 carbon atoms, more preferably, 8 to 20 carbon atoms, said chain being saturated or unsaturated, linear or branched. Sodium is shown as the cation in the above formula (III) but the cation may be an alkali metal ion such as sodium or potassium, ammonium ions, or alkanolammonium ions such as monoethanolammonium or triethanolammonium ions. In some instances, the alkyl sulfonate(s) are selected from $C_8$-$C_{16}$ alkyl benzene sulfonates, $C_{10}$-$C_{20}$ paraffin sulfonates, $C_{10}$-$C_{24}$ olefin sulfonates, salts thereof, and combinations thereof. $C_{10}$-$C_{24}$ olefin sulfonates are particularly preferred. A non-limiting but particularly useful example of a $C_{10}$-$C_{24}$ olefin sulfonate that can be used in the instant compositions is sodium C14-16 olefin sulfonate.

The total amount of the one or more alkyl sulfonates in the solidified gel, if present, will vary but is typically about 0.01 to about 10 wt. %, based on the total weight of the solidified gel. In further embodiments, the solidified gel includes about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, or about 0.5 to about 3 wt. % of one or more alkyl sulfonates, based on the total weight of the solidified gel.

(ii-f) Acyl Isethionates

Non-limiting examples of useful acyl isethionates include those of formula (VII) and (VIII):

(VII)

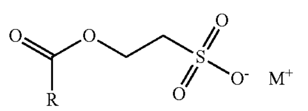

(VIII)

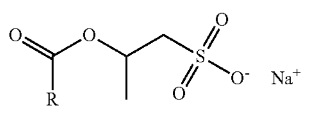

wherein R, $R^1$, $R^2$ and $R^3$ are each independently selected from H or an alkyl chain having 1-24 carbon atoms, said chain being saturated or unsaturated, linear or branched, and X is $COO^-$ or $SO_3^-$. Sodium is shown as the cation in formula (VI) but the cation for both formula (V) and formula (VI) may be an alkali metal ion such as sodium or potassium, ammonium ions, or alkanolammonium ions such as monoethanolammonium or triethanolammonium ions. Non-limiting examples of acyl isethionates include sodium isethionate, sodium cocoyl isethionate, sodium lauroyl methyl isethionate, and sodium cocoyl methyl isethionate. In some instances, sodium cocoyl methyl isethionate is a particularly useful acyl isethionate that may be included in the cleansing compositions.

The total amount of the one or more alkyl isethionates in the solidified gel, if present, will vary but is typically about 0.01 to about 10 wt. %, based on the total weight of the solidified gel. In further embodiments, the solidified gel includes about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, or about 0.5 to about 3 wt. % of one or more alkyl isethionates, based on the total weight of the solidified gel.

(ii-g) Alkyl Sulfosuccinates

Non-limiting examples of useful alkyl sulfosuccinates include those of formula (IX):

(IX)

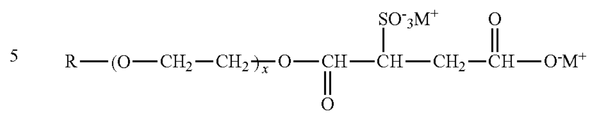

wherein R is a straight or branched chain alkyl or alkenyl group having 10 to 22 carbon atoms, preferably 10 to 20 carbon atoms, X is a number that represents the average degree of ethoxylation and can range from 0 to about 5, preferably from 0 to about 4, and most preferably from about 2 to about 3.5, and M and M' are monovalent cations which can be the same or different from each other. Preferred cations are alkali metal ions such as sodium or potassium, ammonium ions, or alkanolammonium ions such as monoethanolammonium or triethanolammonium ions.

Non-limiting examples of alkyl sulfosuccinates salts include disodium oleamido MIPA sulfosuccinate, disodium oleamido MEA sulfosuccinate, disodium lauryl sulfosuccinate, disodium laureth sulfosuccinate, diammonium lauryl sulfosuccinate, diammonium laureth sulfosuccinate, dioctyl sodium sulfosuccinate, disodium oleamide MEA sulfosuccinate, sodium dialkyl sulfosuccinate, and a combination thereof. In some instances, disodium laureth sulfosuccinate is particularly preferred.

The total amount of the one or more alkyl sulfosuccinates in the solidified gel, if present, will vary but is typically about 0.01 to about 10 wt. %, based on the total weight of the solidified gel. In further embodiments, the solidified gel includes about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, or about 0.5 to about 3 wt. % of one or more alkyl sulfosuccinates, based on the total weight of the solidified gel.

(ii-h) Alkyl Sulfoacetates

Nonlimiting examples of alkyl sulfacetates includes, for example, alkyl sulfoacetates such as C4-C18 fatty alcohol sulfoacetates and/or salts thereof. A particularly preferred sulfoacetate salt is sodium lauryl sulfoacetate. Useful cations for the salts include alkali metal ions such as sodium or potassium, ammonium ions, or alkanolammonium ions such as monoethanolammonium or triethanolammonium ions.

The total amount of the one or more alkyl sulfacetates in the solidified gel, if present, will vary but is typically about 0.01 to about 10 wt. %, based on the total weight of the solidified gel. In further embodiments, the solidified gel includes about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, or about 0.5 to about 3 wt. % of one or more alkyl sulfoacetates, based on the total weight of the solidified gel.

(ii-i) Alkoxylated Monoacids

Non-limiting examples of alkoxylated monoacids include compounds corresponding to formula (X):

(X)

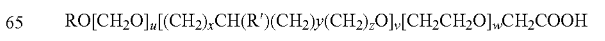

$$RO[CH_2O]_u[(CH_2)_xCH(R')(CH_2)y(CH_2)_zO]_v[CH_2CH_2O]_wCH_2COOH$$

wherein R is a hydrocarbon radical containing from about 6 to about 40 carbon atoms; u, v and w, independently of one another, represent numbers of from 0 to 60; x, y and z, independently of one another, represent numbers of from 0 to 13; R' represents hydrogen or alkyl; and the sum of x+y+z>0.

Compounds corresponding to formula (X) can be obtained by alkoxylation of alcohols ROH with ethylene oxide as the sole alkoxide or with several alkoxides and subsequent oxidation. The numbers u, v, and w each represent the degree of alkoxylation. Whereas, on a molecular level, the numbers u, v and w and the total degree of alkoxylation can only be integers, including zero, on a macroscopic level they are mean values in the form of broken numbers.

In formula (X), R is linear or branched, acyclic or cyclic, saturated or unsaturated, aliphatic or aromatic, substituted or unsubstituted. Typically, R is a linear or branched, acyclic C6-40 alkyl or alkenyl group or a C1-40 alkyl phenyl group, more typically a C8-22 alkyl or alkenyl group or a C4-18 alkyl phenyl group, and even more typically a C12-18 alkyl group or alkenyl group or a C6-16 alkyl phenyl group; u, v, w, independently of one another, is typically a number from 2 to 20, more typically a number from 3 to 17 and most typically a number from 5 to 15; x, y, z, independently of one another, is typically a number from 2 to 13, more typically a number from 1 to 10 and most typically a number from 0 to 8.

Suitable alkoxylated monoacids include, but are not limited to: Butoxynol-5 Carboxylic Acid, Butoxynol-19 Carboxylic Acid, Capryleth-4 Carboxylic Acid, Capryleth-6 Carboxylic Acid, Capryleth-9 Carboxylic Acid, Ceteareth-25 Carboxylic Acid, Coceth-7 Carboxylic Acid, C9-11 Pareth-6 Carboxylic Acid, C11-15 Pareth-7 Carboxylic Acid, C12-13 Pareth-5 Carboxylic Acid, C12-13 Pareth-8 Carboxylic Acid, C12-13 Pareth-12 Carboxylic Acid, C12-15 Pareth-7 Carboxylic Acid, C12-15 Pareth-8 Carboxylic Acid, C14-15 Pareth-8 Carboxylic Acid, Deceth-7 Carboxylic Acid, Laureth-3 Carboxylic Acid, Laureth-4 Carboxylic Acid, Laureth-5 Carboxylic Acid, Laureth-6 Carboxylic Acid, Laureth-8 Carboxylic Acid, Laureth-10 Carboxylic Acid, Laureth-11 Carboxylic Acid, Laureth-12 Carboxylic Acid, Laureth-13 Carboxylic Acid, Laureth-14 Carboxylic Acid, Laureth-17 Carboxylic Acid, PPG-6-Laureth-6 Carboxylic Acid, PPG-8-Steareth-7 Carboxylic Acid, Myreth-3 Carboxylic Acid, Myreth-5 Carboxylic Acid, Nonoxynol-5 Carboxylic Acid, Nonoxynol-8 Carboxylic Acid, Nonoxynol-10 Carboxylic Acid, Octeth-3 Carboxylic Acid, Octoxynol-20 Carboxylic Acid, Oleth-3 Carboxylic Acid, Oleth-6 Carboxylic Acid, Oleth-10 Carboxylic Acid, PPG-3-Deceth-2 Carboxylic Acid, Capryleth-2 Carboxylic Acid, Ceteth-13 Carboxylic Acid, Deceth-2 Carboxylic Acid, Hexeth-4 Carboxylic Acid, Isosteareth-6 Carboxylic Acid, Isosteareth-11 Carboxylic Acid, Trudeceth-3 Carboxylic Acid, Trideceth-6 Carboxylic Acid, Trideceth-8 Carboxylic Acid, Trideceth-12 Carboxylic Acid, Trideceth-3 Carboxylic Acid, Trideceth-4 Carboxylic Acid, Trideceth-7 Carboxylic Acid, Trideceth-15 Carboxylic Acid, Trideceth-19 Carboxylic Acid, Undeceth-5 Carboxylic Acid and combinations thereof. In some cases, preferred ethoxylated acids include Oleth-10 Carboxylic Acid, Laureth-5 Carboxylic Acid, Laureth-11 Carboxylic Acid, and a combination thereof.

The total amount of the one or more alkoxylated monoacids in the solidified gel, if present, will vary but is typically about 0.01 to about 10 wt. %, based on the total weight of the solidified gel. In further embodiments, the solidified gel includes about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 0.5 to about 10 wt. %, about 0.5 to about 8 wt. %, about 0.5 to about 5 wt. %, or about 0.5 to about 3 wt. % of one or more alkoxylated monoacids, based on the total weight of the solidified gel.

(c)(iv) Cationic Surfactants

The solidified gel may include one or more cationic surfactants. The term "cationic surfactant" is a surfactant that may be positively charged when contained in the solidified gel. The cationic surfactant may bear one or more positive permanent charges or may contain one or more functional groups that are cationizable in the composition according to the disclosure. The solidified gels do not require cationic surfactants. When the solidified gel includes one or more anionic surfactants, it is preferably that the solidified gel be free or essentially free from cationic surfactants. Therefore, in various preferred embodiments, the solidified gel is free or essentially free from cationic surfactants.

Nonlimiting examples of cationic surfactants include cetrimonium chloride, stearimonium chloride, behentrimonium chloride, behentrimonium methosulfate, behenamidopropyltrimonium methosulfate, stearamidopropyltrimonium chloride, arachidtrimonium chloride, distearyldimonium chloride, dicetyldimonium chloride, tricetylmonium chloride, oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, palmitamidopropyl dimethylamine, and mixtures thereof.

Cationic surfactants include polyoxyalkylenated, primary, secondary or tertiary fatty amines, or salts thereof, and quaternary ammonium salts, and mixtures thereof, for example, chloride salts of quaternary ammonium compounds. The fatty amines generally comprise at least one $C_8$-$C_{30}$ hydrocarbon-based chain.

Nonlimiting examples of cationizable cationic surfactants include stearyloxypropyl amine, palmityloxypropyl amine, stearyloxypropyldimethyl amine, stearyloxypropyldiethyl amine, stearyloxyethylyldimethyl amine, stearyloxyethyl amine, myristyloxypropyl amine, myristyloxypropyldimethyl amine, palmitamidopropyl amine, palmitamidopropyl methylamine, palmitamidopropyl diethylamine, palmitamidopropyl dibutylamine, palmitamidopropyl butylamine, palmitamidopropyl dipropylamine, palmitamidopropyl propylamine, palmitamidopropyl dihydroxyethylamine, palmitamidopropyl hydroxyethylamine, palmitamidopropyl dihydroxypropylamine, palmitamidopropyl hydroxypropylamine, lauramidopropyl amine, lauramidopropyl methylamine, lauramidopropyl diethylamine, lauramidopropyl dibutylamine, lauramidopropyl butylamine, lauramidopropyl dipropylamine, lauramidopropyl propylamine, lauramidopropyl dihydroxyethylamine, lauramidopropyl hydroxyethylamine, lauramidopropyl dihydroxypropylamine, lauramidopropyl hydroxypropylamine, stearamidopropyl amine, stearamidopropyl dimethylamine, stearamidopropyl diethylamine, stearamidopropyldibutylamine, stearamidopropyl butylamine, stearamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, behenamidopropyl amine, behenamidopropyl methylamine, behenamidopropyl diethylamine, behenamidopropyl dibutylamine, behenamidopropyl butylamine, behenamidopropyl dipropylamine, behenamidopropyl propylamine, behenamidopropyl dihydroxyethylamine, behenamidopropyl hydroxyethylamine, behenamidopropyl dihydroxypropylamine, behenamidopropyl hydroxypropylamine, dipalmitamidopropyl methylamine, dipalmitamidopropyl ethylamine, dipalmitamidopropyl butylamine, dipalmitamidopropyl propylamine, dipalmitamidopropyl hydroxyethylamine, dipalmitamidopropyl hydroxypropylamine, dilauramidopropyl amine, dilauramidopropyl methylamine, dilauramidopropyl buylamine, dilauramidopropyl hydroxyethylamine, dilauramidopropyl hydroxypropylamine, distearamidopropyl amine, distearamidopropyl methylamine, dibehenamidopropyl propylamine, dibehenamidopropyl hydroxyethylamine, palmitoamidopropyl trimethyl ammonium chloride, stearamidopropyl trimethylammonium chloride, behenamidopropyl tri hydroxyethalmonium chloride, distearylamidopropyl dimethyl ammonium chloride, dicetylamidodihydroxyethyl ammonium chloride, palmitoylpropyl amine, palmitoylpropyl methylamine, palmitoylpropyl diethylamine, palmitoylpropyl dibutylamine, palmitoylpropyl buylamine, palmitoylpropyl dipropylamine, palmitoylpropyl propylamine, palmitoylpropyl dihydroxyethylamine, palmitoylpropyl hydroxyethylamine, palmitoylpropyl dihydroxypropylamine, palmitoylpropyl hydroxypropylamine, myristoylpropyl amine, myristoylpropyl methylamine, myristoylpropyl diethylamine, myristoylpropyl dibutylamine, myristoylpropyl buylamine, myristoylpropyl dipropylamine, myristoylpropyl propylamine, myristoylpropyl dihydroxyethylamine, myristoylpropyl hydroxyethylamine, myristoylpropyl dihydroxypropylamine, myristoylpropyl hydroxypropylamine, stearoylpropyl amine, stearoylpropyl methylamine, stearoylpropyl diethylamine, stearoylpropyl dibutylamine, stearoylpropyl butylamine, stearoylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, behenylpropyl amine, behenylpropyl methylamine, behenylpropyl diethylamine, behenylpropyl dibutylamine, behenylpropyl butylamine, behenylpropyl dipropylamine, behenylpropyl propylamine, behenylpropyl dihydroxyethylamine, behenylpropyl hydroxyethylamine, behenylpropyl dihydroxypropylamine, behenylpropyl hydroxypropylamine, dipalmitoylpropyl methylamine, dipalmitoylpropyl ethylamine, dipalmitylpropyl butylamine, dipalmitylpropyl propylamine, dipalmitylpropyl hydroxyethylamine, dipalmitylpropyl hydroxypropylamine, dilauroylpropyl amine, dilauroylpropyl methylamine, dilauroylpropyl buylamine, dilauroylpropyl hydroxyethylamine, dilauroylpropyl hydroxypropylamine, distearylpropyl amine, distearylpropyl methylamine, dibehenylpropyl propylamine, and dibehenylpropyl hydroxyethylamine.

Cationizable surfactants may be chosen from fatty alkylamines and fatty dialkylamines. Preferable fatty dialkylamines include fatty amidoamine compounds, their salts, and mixtures thereof. Nonlimiting examples include oleamidopropyl dimethylamine, linoleamidopropyl dimethylamine, isostearamidopropyl dimethylamine, oleyl hydroxyethyl imidazoline, stearamidopropyldimethylamine, behenamidopropyldimethylamine, behenamidopropyldiethylamine, behenamidoethyldiethyl-amine, behenamidoethyldimethylamine, arachidamidopropyldimethylamine, arachidamido-propyidiethylamine, arachidamidoethyidiethylamine, arachidamidoethyidimethylamine, brassicamidopropyldimethylamine, lauramidopropyl dimethylamine, myristamidopropyl dimethylamine, dilinoleamidopropyl dimethylamine, and palmitamidopropyl dimethylamine.

The total amount of the one or more cationic surfactants, if present, will vary but is typically about 0.01 to about 5 wt. %, based on the total weight of the solidified gel. In further embodiments, the solidified gel includes about 0.01 to about 3 wt. %, about 0.01 to about 2 wt. %, about 0.01 to about 1 wt. %, about 0.05 to about 5 wt. %, about 0.05 to about 3 wt. %, about 0.05 to about 2 wt. %, about 0.05 to about 1 wt. %, about 0.1 to about 5 wt. %, about 0.1 to about 3 wt. %, about 0.1 to about 2 wt. %, or about 0.1 to about 1 wt. % of one or more cationic surfactants, based on the total weight of the solidified gel.

(e) Water

The total amount of water in the solidified gel will vary but is typically about 70 to about 95 wt. %, based on the total weight of the solidified gel. In further embodiments, the solidified gel includes about 75 to about 95 wt. %, about 80 to about 95 wt. %, about 85 to about 95 wt. %, about 88 to about 95 wt. %, about 90 to about 95 wt. %, or about 88 to about 94 wt. %, based on the total weight of the solidified gel. Preferably, the solidified gel includes about 75 to about 95 wt. %, preferably about 80 to about 95 wt. %, and even more preferably about 85 to about 95 wt. %, based on the total weight of the solidified gel.

(f) Miscellaneous Ingredients

The solidified gel may include one or more miscellaneous ingredients. Miscellaneous ingredients are ingredients that are compatible with the solidified gel and do not disrupt or materially affect the basic and novel properties of the solidified gel. Miscellaneous ingredients commonly used in cosmetics are known in the art. Nonlimiting examples include preservatives, fragrances, pH adjusters, salts, chelating agents, buffers, antioxidants, flavonoids, vitamins, botanical extracts, UV filtering agents, proteins, protein hydrolysates, emollients, humectants, hydrotropes, fillers (e.g., organic or inorganic, such as talk, calcium carbonate, dextrin, silica, etc.), pearlescent agents, composition colorants, essential oils, etc.

In the context of the instant disclosure, a "composition colorant" is a compound that colors the composition but does not have an appreciable coloring effect on skin. In other words, the composition colorant is included to provide a coloring to the solidified gel for aesthetic appeal but is not intended to impart coloring properties to the skin.

In addition to the nonlimiting list of miscellaneous ingredients set forth above, components described throughout the instant disclosure may be characterized as miscellaneous ingredients if not expressly set forth as a required component of the solidified gel. Thus, the term "miscellaneous ingredient" is understood as a catch-all phrase representing additional components that may optionally be present in amounts designated for the miscellaneous ingredients.

The total amount of miscellaneous ingredients in the solidified gel, if present, will vary. Nonetheless, the solidified gel typically includes from about 0.01 to about 10 wt. % of one or more miscellaneous ingredients, based on the total weight of the solidified gel. In further embodiments, the solidified gel includes about 0.01 to about 8 wt. %, about 0.01 to about 5 wt. %, about 0.01 to about 3 wt. %, about 0.1 to about 10 wt. %, about 0.1 to about 8 wt. %, about 0.1 to about 5 wt. %, about 0.1 to about 3 wt. %, about 1 to about 10 wt. %, about 1 to about 8 wt. %, about 1 to about 5 wt.

%, or about 1 to about 3 wt. % of one or more miscellaneous ingredients, based on the total weight of the solidified gel.

The solidified gel may include one or more essential oils. The one or more essential oils can be characterized as a miscellaneous ingredient or characterized as an independent elements of the solidified gel. Essential oils are concentrated liquid extracts of aromatic plants, typically in the form of volatile oils containing compounds that give plants their characteristic odors and therapeutic properties. Distillation involves passing water vapor through the plant, causing the aromatic compounds to evaporate. The vapor is then cooled and condensed, separating the essential oil from the water. Essential oils come from various parts of plants, such as flowers, leaves, bark, roots, or fruit. For example, lavender essential oil is extracted from the flowers, lemon essential oil is extracted from the zest, and ginger essential oil is extracted from the rhizome. Essential oils have a unique composition of chemicals that can vary within the same plant species, or from plant to plant.

For purposes of the instant disclosure, the term "essential oil" is used in accordance with The European Pharmacopoeia; and essential oils can be identified and characterized according to Do et al., *Proposal for a standardised method for the identification of essential oils by HPTLC*, Pharmeur. Bio. Sci. Notes. 2021; 2021:157-166 (PMID: 34751647), which are incorporated herein by reference in their entirety.

Nonlimiting examples of essential oils include lavender oil, geranium oil, juniper berry oil, bay leaf oil, lemon oil (or lemon peel oil), mandarin orange oil, orange oil, absinthe oil, African bluegrass oil, ajowan oil, anethi oil, angelica root oil, anise star oil, arborvitae wild oil, armoise mugwort oil, asafetida oil, Australian balm oil, basil oil, benzoin oil, bergamot calabrian oil, betel leaf oil, birch sweet oil, birch tar oil, black currant-seed oil, blood orange oil, buchu oil, cabreuva oil, cade oil, cajeput oil, calamus root oil, camphor oil, cananga oil, caraway oil, cardamom oil, carrotseed oil, cassia oil, cedarleaf oil cedarwood atles oil, cedarwood Chinese oil, cedarwood Himalayan oil, cedarwood texas oil, cedarwood Virginian oil, celery seed oil, chamomile German oil, chamomile moroc oil, chamomile roman oil, chaulmogra oil, chenopodium oil, chilly seed oil, cinnamon bark oil, cinnamon leaf oil, citral oil, citronelia Ceylon oil, clarysage oil, clementine oil, clove bud oil, clove leaf oil, cognac oil, copaiba balsam oil, coriander oil, costus root oil, coffee oil, cumin oil, curcuma oil, curry leaf oil, cypress Australian blue oil, cypress French cypriol oil, davana oil, dill seed oil, dill weed oil, elemi oil, emu oil, eucalyptus oil, fennel bitter oil, fenugreek oil, fir balsam oil, fir needle oil, flax seed organic oil, frankincense oil garlic oil, galbanum oil, ginger oil, ginger grass oil, gaia oil, grapefruit pink oil, grapefruit white oil, guaiacwood oil, helichrysum oil, horseradish oil, hydacheim oil, hyssop oil, jamarosa root oil, Himalayan wild oil, karanj seed oil, kanuka oil, katrafay oil, key lime oil, kunzea oil, kukuinut oil, lantana oil, laurel leaf oil, lemongrass oil, lemon eucalyptus oil, lemon myrtle oil, lemon 5 fold oil, lican oil, lime oil, litsea cubeba oil, lovage leaf oil, mace oil, mandarin oil, manuka oil, marjoram oil, Melissa leaf oil, menthol liquid oil, mullein oil, myrrh oil, myrtle oil, neem oil, neroli oil, nerolina Australian oil, niaouli oil, noni oil, nutmeg oil, oat oil, onion oil, opoponax oil, orange bitter oil, orange sweet oil, origanum oil, orange 5 fold oil, palmarosa oil, parsley oil, patchouli oil, pennyroyal oil, pepper oil, peppermint oil, peru balsam oil, petitgrain oil, pimento leaf oil, pine long leaf oil, pine scotch oil, pine commercial oil, pomegranate oil, pomouwood oil, ravensara wild oil, rosalina Australian oil, rose geranium oil, rosemary oil, rosewood oil, rue oil, sage Dalmatian oil, sandalwood oil, savine oil, savory winter oil, sea buckthorn oil, spearmint oil, spikenard oil, spruce oil, sugandh kokila oil, sumac oil, tagetes oil, tangerine oil, tansy blue oil, tarragon oil, tangerine 5 fold oil, tea tree oil, tea tree lemon oil, thyme oil, tolu balsam oil, turmeric oil, valerian root oil, vanilla 10 fold oil, vetivewr oil, wintergreen oil, wild verbena oil, wormwood oil, yarrow oil, ylang ylang oil, or combinations thereof.

In a preferred embodiment, the solidified gel includes at least one essential oils selected from lemon oil, mandarin orange oil, orange oil, lavender oil, peppermint oil, rosemary oil, tea tree oil, Roman chamomile oil, bergamot oil, jasmine oil, Ylang-ylang oil, eucalyptus oil, geranium oil, patchouli oil, frankincense oil, lemongrass oil, cedarwood, grapefruit oil, or combinations thereof.

The total amount of the one or more essential oils in the solidified gel, if present, will vary but is typically about 0.01 to about 5 wt. %, based on the total weight of the solidified gel. In further embodiments, the solidified gel includes about 0.01 to about 4 wt. %, about 0.01 to about 3 wt. %, about 0.01 to about 2 wt. %, about 0.01 to about 1 wt. %, about 0.05 to about 5 wt. %, about 0.05 to about 4 wt. %, about 0.05 to about 3 wt. %, about 0.05 to about 2 wt. %, or about 0.05 to about 1 wt. %, based on the total weight of the solidified gel.

Hardness

The hardness of the solidified gel will vary but is typically about 2 N (Newtons) or about 200 gram-force, at 25° C. In further embodiments, the hardness of the solidified gel is about 2 to about 15 N, about 2 to about 12 N, about 2 to about 10 N, about 2 to about 5 N, about 3 to about 20 N, about 3 to about 15 N, about 3 to about 12 N, about 3 to about 10 N, about 3 to about 5 N, about 5 to about 20 N, about 5 to about 15 N, about 5 to about 12 N, about 5 to about 10 N at 25° C. The hardness may also be from about 200 to about 1,500 gram-force, about 200 to about 1,200 gram-force, about 200 to about 1,000 gram-force, about 300 to about 1,500 gram-force, about 300 to about 1,200 gram-force, about 300 to about 1,000 gram-force, about 400 to about 1,500 gram-force, about 400 to about 1,200 gram-force, about 400 to about 1,000 gram-force, about 500 to about 1,500 gram-force, about 500 to about 1,200 gram-force, about 500 to about 1,000 gram-force at 25° C.

The hardness of the solidified gel can be measured by penetration of a probe into the composition using a texture analyzer (for example TA-XT2 from Rheo) equipped with a stainless-steel ball. The hardness measurement is carried out at 25° C. at the center of 5 samples of the composition. The ball penetrates into each sample to a distance of 5 mm, at a speed of 0.5 mm/s, after which it is removed from the sample at a speed of 2 mm/s. The force exerted by the sample on the measuring body is recorded continuously. The maximum force is detected at the end of the penetration phase. This force value reflects the hardness of the sample.

Transparency

The solidified gel is typically transparent or translucent. Preferably, the solidified gel is transparent. The term "transparent" with respect to a transparent solidified gel indicates that the composition has transmittance of at least 80% at a wavelength of 600 nm, for example measured using a Lambda 40 UV-visible spectrometer. The solidified gel may have, for example, a transmittance of at least 80%, at least 90%, or at least 95% at a wavelength of 600 nm, measured, for example, using a Lambda 40 UV-visible spectrometer. The term "clear" is interchangeable with the term "transparent" for purposes of the instant disclosure. A human can typically see through a transparent composition, for example, and read the text on the other side of a clear glass or clear plastic bottle containing the solidified gel.

The term "translucent" with respect to a translucent solidified gel indicates that the solidified gel has a transmittance of at least 50% at a wavelength of 600 nm, for example measured using a Lambda 40 UV-visible spectrometer. A human cannot likely see through a translucent solidified gel, for example, and cannot read the text on the other side of a clear glass or clear plastic bottle containing the solidified gel. Rather, the text is usually blurred and difficult or not possible to read, yet movement and structure can normally be identified.

The term "opaque" with respect to an opaque solidified gel indicates that the solidified gel is not transparent or translucent, i.e., has a transmittance of less than 50% at a wavelength of 600 nm, for example measured using a Lambda 40 UV-visible spectrometer.

Shaving Cap

The shaving cap may be an independent structure or it may be integrated with a closing cap, i.e., a cap for closing the dispensing opening of the container housing the solidified gel. The FIGURE shows a container (6) with a screw cap (4) and a cutting device (3). The shaving cap (3) is shown to be removably integrated with the screw cap (4). The cutting device (3), however, is preferably separable from the screw cap (4) and can independently be used to shave an exposed surface of the solidified gel. The solidified gel (not shown) is contained inside container (6), which has a dispensing opening (10) which exposes an outer surface of the solidified gel contained inside the container (6). When the screw cap (4) is removed from the container (6) the solidified gel can be expelled through the dispensing opening. Shaving cap (3) can be applied over the exposed surface of the solidified gel and used to shave at least part of the solidified gel away from a mass of solidified gel inside the container (6), for example, by twisting the shaving cap (3) over the exposed surface of the solidified gel. As the solidified gel is shaved by the shaving cap (3), shavings of the solidified gel are expelled through the openings (1) shown as slits.

Container

Various different types and shapes of containers are suitable for use in accordance with the instant disclosure. In various embodiments, a tube-like container is particularly useful, i.e., a container having a tube shape or cylindrical shape with a closed bottom end and an opening on the opposite end. Further, a particularly useful container includes a twist-up mechanism. A rotatable handwheel is provided at the closed bottom end to drive an elevator or advancing mechanism to advance the mass of solidified gel inside the container toward the dispensing end (open end) of the container. The handwheel is rotated so that a desired portion of the solidified gel protrudes beyond the dispensing end. When the exposed end of the solidified gel is drawn across the exposed surface, a layer of product is shaved away from the mass of solidified gel. The thickness of the layer that is shaved away is controlled by a number of factors, including the texture of the desired surface, the viscosity or abrasion-resistance of the product, the width of the mass of solidified gel in the direction normal to the application direction, etc.

The FIGURE shows a container (6) with a screw cap (4) and a cutting device (3). Container (6) houses a mass of solidified gel and contains a dispensing opening (10). The container (6) is shown as a tube but the shape of the container is not limited. Nonetheless, the container (6) typically includes a closed end opposite a dispensing opening (10). The container (6) optionally includes a cap (4) such as a screw cap or slide cap to close the container (6) with the solidified gel contained therein. When cap (4) is a screw cap, it includes threads on the inside of the cap to engage with a threaded container rim (5). The container (6) may also optionally include a threaded post (14), a support platform (8), and a wheel (9), which allows a consumer to expel at least part of the solidified gel from the container (6) by rotating the wheel (9).

In various embodiments, the container is a tube-type container with an advancing mechanism, for example, like set forth in US2012/0093565, which is incorporated herein by reference in its entirety. In further embodiments, the container is a twist-up container, for example, like set forth in U.S. Pat. No. 5,547,302, which is incorporated herein by reference in its entirety.

Preferred Embodiments

The solidified gel preferably includes little or no oil or other fatty compounds. Nonetheless, the solidified gel may include small amounts of one or more oils or fatty compounds, including one or more essential oils. An "oil" is a fatty compound excluding silicones that is a liquid a room temperature and atmospheric pressure (25° C., 1 atm). When one or more oils is present, the total amount of the one or more oils is typically less than 5 wt. %, based on the total weight of the solidified gel. In further embodiments, if the solidified gel comprises one or more oils, the total amount of the oils less than 3 wt. %, less than 2 wt. %, less than 1 wt. %, less than 0.5 wt. %, or less than 0.2 wt. %, based on the total weight of the solidified gel. In various embodiments, the solidified gel includes no oil or an amount of oil from about 0.01 to about 3 wt. %, about 0.01 to about 2 wt. %, about 0.01 to 1.5 wt. %, about 0.01 to about 1 wt. %, about 0.01 to about 0.8 wt. %, about 0.05 to about 3 wt. %, about 0.05 to about 2 wt. %, about 0.05 to about 1.5 wt. %, about 0.05 to about 1 wt. %, about 0.05 to about 0.8 wt. %, about 0.1 to about 3 wt. %, about 0.1 to about 2 wt. %, about 0.1 to about 1.5 wt. %, about 0.1 to about 1 wt. %, or about 0.1 to about 0.8 wt. %, based on the total weight of the solidified gel. Preferably, if present, the total amount of oil in the solidified gel is from about 0.01 to about 3 wt. %, preferably about 0.05 to about 2 wt. %, and even more preferably about 0.05 to about 1 wt. %, based on the total weight of the solidified gel.

The solidified gel does not require fatty compounds. Therefore, the solidified gel may be free or essentially free from fatty compounds. The term "fatty compounds" (also referred to as "lipids") refers to organic molecules that are largely nonpolar and hydrophobic, meaning they do not mix well with water. Fatty compounds are a diverse group of compounds that include fats, oils, waxes, and the like. Thus, the oils discussed above are a type of fatty compound. Although fatty compounds are not required, one or more fatty compounds may nonetheless be included in the solidified gel. When one or more fatty compounds is present, the total amount of the one or more fatty compounds is typically less than 5 wt. %, based on the total weight of the solidified gel. In further embodiments, if the solidified gel comprises one or more fatty compounds, the total amount of the fatty compounds is less than 3 wt. %, less than 2 wt. %, less than 1 wt. %, less than 0.5 wt. %, or less than 0.2 wt. %, based on the total weight of the solidified gel. In various embodiments, the solidified gel includes no fatty compounds or an amount of fatty compounds from about 0.01 to about 3 wt. %, about 0.01 to about 2 wt. %, about 0.01 to 1.5 wt. %, about 0.01 to about 1 wt. %, about 0.01 to about 0.8 wt. %, about 0.05 to about 3 wt. %, about 0.05 to about 2 wt. %, about 0.05 to about 1.5 wt. %, about 0.05 to about 1 wt. %, about 0.05 to about 0.8 wt. %, about 0.1 to about 3 wt. %, about 0.1 to about 2 wt. %, about 0.1 to about 1.5 wt. %, about 0.1 to about 1 wt. %, or about 0.1 to about 0.8 wt. %, based on the total weight of the solidified gel. Preferably, if present, the total amount of fatty compounds in the solidified gel is from about 0.01 to about 3 wt. %, preferably about 0.05 to about 2 wt. %, and even more preferably about 0.05 to about 1 wt. %, based on the total weight of the solidified gel.

The solidified gel does not require silicones, including amino-functionalized silicones. Therefore, in a preferred embodiment, the solidified gel is free or essentially free from silicones, including amino-functionalized silicones. In other embodiments, one or more silicones may optionally be included the solidified gel. Nonlimiting examples of silicones that are not amino-functionalized silicone oils include dimethicone, dimethiconol, cyclomethicone, polysilicone-11, phenyl trimethicone, and stearoxytrimethylsilane. Nonlimiting examples of amino-functionalized silicones include amodimethicone, bis-aminopropyl dimethicone, and trimethyl silylamodimethicone.

In various embodiments, the solidified gel includes one or more anionic surfactants. Anionic surfactants include sulfates (or "sulfate surfactants"). In a preferred embodiment, the solidified gel includes one or more anionic surfactants other than sulfates (or sulfate surfactants) and is free or essentially free from sulfates (or sulfate surfactants).

The solidified gel does not require cationic surfactants. In various embodiments, one or more cationic surfactants may be included in the solidified gel. Nonetheless, in a preferred embodiment, the solidified gel is free or essentially free from cationic surfactants.

The solidified gel does not require cationic polymers, including cationic conditioning polymers. In various embodiments, one or more cationic polymers including one or more cationic conditioning polymers, may be included in the solidified gel. Nonlimiting examples of cationic polymers include polyquaterniums, e.g., polyquaternium-6, polyquaternium-7, polyquaternium-10, polyquaternium-11, polyquaternium-37, and the like. Nonetheless, in a preferred embodiment, the solidified gel is free or essentially free from cationic polymers including cationic conditioning polymers.

The solidified gel includes a large amount of water, which is gelled or solidified using gellan gum. Additional thickening agents are not required. The term "thickening agent" may interchangeably be referred to as "thickener" or "viscosity modifying agent." Although not required, in various embodiments, the solidified gel includes one or more additional thickening agents. Nonlimiting examples include additional polysaccharide thickening agents and non-polysaccharide polymeric thickening agents. In a preferred embodiment, the solidified gel is free or essentially free from thickening agents other than the gellan gum. In other embodiments, the solidified gel is free or essentially free from polysaccharide thickening agents (other than the gellan gum) but optionally includes one or more non-polysaccharide thickening agents, for example, one or more non-polysaccharide polymeric thickening agents.

Nonlimiting examples of non-polysaccharide polymeric thickening agents include: (a) vinylpyrrolidone and copolymers of vinylpyrrolidone such as vinylpyrrolidone/hexadecene copolymer and vinylpyrrolidone/eicosene copolymer; (b) acrylates, methacrylates, and copolymers thereof, for example, copolymers of $C_1$-$C_6$ alkyl methacrylates or acrylates and of amphiphilic monomers comprising at least one fatty chain, for instance the oxyethylenated methyl acrylate/stearyl acrylate copolymer; (c) copolymers of hydrophilic methacrylates or acrylates and of hydrophobic monomers comprising at least one fatty chain, for instance the polyethylene glycol methacrylate/lauryl methacrylate copolymer; (d) polyurethanes and polyurethane polyethers, for example polyurethane polyethers comprising in their chain both hydrophilic blocks usually of polyoxyethylenated nature and hydrophobic blocks, which may be aliphatic sequences alone and/or cycloaliphatic and/or aromatic sequences; (e) taurate copolymers, for example, acrylamide/sodium acryloyl dimethyl taurate copolymer, hydroxyethyl acrylate/sodium acryloyl dimethyl taurate copolymer, ammonium acryloyldimethyl taurate/VP copolymer, sodium acrylate/sodium acryloyl dimethyl taurate copolymer, and hydroxyethyl acrylate/sodium acryloyldimethyl taurate copolymer; and (f) polyacrylic acid thickening agents including crosslinked polyacrylic acid thickening agents and copolymers of acrylic acid.

Nonlimiting examples of polysaccharide thickening agents, other than gellan gum, include xanthan gum and xanthan derivatives (e.g., dehydroxanthan gum), cellulose and cellulose derivatives (e.g., hydroxypropyl cellulose), guar gum and guar derivatives (guar hydroxypropyltrimonium chloride), sclerotium gum and sclerotium derivatives, acacia Senegal gum, and the like.

The solidified gel does not require $C_1$-$C_6$ monoalcohols such as ethanol and isopropanol. Nonetheless, $C_1$-$C_6$ monoalcohols may be included in the solidified gel. In a preferred embodiment, however, the solidified gel is free or essentially free from ethanol, free or essentially free from isopropanol, or free or essentially free from both ethanol and isopropanol. In a further embodiment, the solidified gel is preferably free or essentially free from $C_1$-$C_6$ monoalcohols. In another embodiment, if one or more $C_1$-$C_6$ monoalcohols are present, they are typically in an amount of about 0.01 to about 5 wt. %, based on the total weight of the solidified gel. In further embodiments, the solidified gel includes about 0.01 to about 3 wt. %, about 0.01 to about 1 wt. %, about 0.01 to about 0.5 wt. %, about 0.1 to about 5 wt. %, about 0.1 to about 3 wt. %, about 0.1 to about 2 wt. %, about 0.1 to about 1 wt. % of the one or more $C_1$-$C_6$ monoalcohols, based on the total weight of the solidified gel.

In a preferred embodiment, the cosmetic kit includes a container housing the solidified gel and a shaving cap, wherein the solidified gel comprises, consists essentially of, or consists of:

(a) about 1.2 wt. % or more, preferably about 1.32 to about 3 wt. %, more preferably about 1.3 to about 2 wt. %, and even more preferably about 1.5 to about 2 wt. % of gellan gum;

(b) about 1 to about 15 wt. %, preferably about 2 to about 12 wt. %, and more preferably about 2 to about 8 wt. % of one or more polyols having from 2 to 10 carbon atoms, wherein the one or more polyols are preferably selected from ethylene glycol, propylene glycol, butylene glycol, hexylene glycol, pentylene glycol, 1,3-propanediol, diethylene glycol, dipropylene glycol, caprylyl glycol, glycerin, or mixtures thereof, wherein the solidified gel preferably includes two or more polyols having from 2 to 10 carbon atoms, wherein one of the two or more polyols having from 2 to 10 carbon atoms is preferably glycerin;

(c) about 0.5 to about 15 wt. %, preferably about 1 to about 10 wt. %, more preferably about 2 to about 6 wt. % of one or more surfactants selected from amphoteric surfactants, nonionic surfactants, anionic surfactants, and cationic surfactants, wherein the anhydrous composition preferably comprises a plurality of surfactants, wherein the plurality of surfactants includes one or more amphoteric surfactants, one or more nonionic surfactants, and optionally, one or more anionic surfactants, wherein preferably, the one or more amphoteric surfactants are selected from alkyl amphopropriionates, betaines, alkyl sultaines, alkyl amphoacetates, or mixtures thereof;

(d) about 75 to about 95 wt. %, preferably about 80 to about 95 wt. %, even more preferably about 85 to about 95 wt. % of water;

(e) optionally, about 0.01 to about 10 wt. %, preferably about 0.1 to about 8 wt. %, and more preferably about 1 to about 6 wt. % of one or more miscellaneous ingredients, wherein the one or more miscellaneous ingredients are selected from preservatives, fragrances, essential oils, chelating agents, antioxidants, flavonoids, vitamins, botanical extracts, UV filtering agents, proteins, protein hydrolysates, protein isolates, fillers, composition colorants, or mixtures thereof;

the solidified gel transparent or translucent, preferably transparent, and all weight percentages are based on a total weight of the solidified gel.

As noted above, the solidified gel preferably includes a plurality of surfactants. The plurality of surfactants preferably comprises, consists essentially of, or consists of:

(c)(i) about 0.1 to about 8 wt. %, preferably about 0.5 to about 5 wt. %, and more preferably about 1 to about 4 wt. % of one or more amphoteric surfactants, wherein at least one of the one or more amphoteric surfactants is an alkyl amphoacetate, preferably wherein the alkyl amphoacetate is selected from disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylampho-dipropionate, disodium caprylomphodipropionate, lauroamphodipropionic acid, cocoamphodipropionic acid, or mixtures thereof;

(c)(ii) about 0.1 to about 8 wt. %, preferably about 0.2 to about 5 wt. %, and more preferably about 0.5 to about 4 wt. % of one or more nonionic surfactants, wherein the one or more nonionic surfactants are preferably selected from poloxamers; polysorbates; alkyl polyglucosides; alcohols, alpha-diols, alkylphenols or esters of fatty acids, being optionally ethoxylated, propoxylated, or glycerolated (polyglyceryl-2 isostearate); ethoxylated fatty esters; glyceryl esters of fatty acids; fatty alcohol ethoxylates; alkyl phenol ethoxylates; fatty acid alkoxylates; and mixtures thereof, wherein at least one of the one or more nonionic surfactants is preferably selected from poloxamers, wherein the poloxamers are preferably selected from poloxamer-101, poloxamer-105, poloxamer-105 benzoate, poloxamer-108, poloxamer-122, poloxamer-123, poloxamer-124, poloxamer-181, poloxamer-182, poloxamer-182 dibenzoate, poloxamer-183, poloxamer-184, poloxamer-185, poloxamer-188, poloxamer-212, poloxamer-215, poloxamer-217, poloxamer-231, poloxamer-234, poloxamer-235, poloxamer-237, poloxamer-238, poloxamer-282, poloxamer-284, poloxamer-288, poloxamer-331, poloxamer-333, poloxamer-334, poloxamer-335, poloxamer-338, poloxamer-401, poloxamer-402, poloxamer-403, and poloxamer-407, or mixtures thereof;

(c)(iii) optionally, about 0.01 to about 8 wt. %, about 0.1 to about 6 wt. %, even more preferably about 0.5 to about 5 wt. % of one or more anionic surfactants, wherein the one or more anionic surfactants are preferably selected form sulfates, acyl isethionates, acyl amino acids (such as acyl taurates, acyl glycinates, acyl glutamates, and acyl sarcosinates), alkyl sulfonates, alkyl sulfosuccinates, alkyl sulfoacetates, alkoxylated monoacids, salts thereof, and a combination thereof;

wherein the plurality of surfactants of the solidified gel is preferably free or essentially free from sulfates; and the plurality of surfactants in the solidified gel is preferably free or essentially free from cationic surfactants.

The solidified gel preferably comprises about 2 wt. % or less of oils. More preferably, the solidified gel comprises about 1.5 wt. % or less of oils. Even more preferably, the solidified gel comprises about 1 wt. % or less of oils.

The solidified gel preferably comprises about 2 wt. % or less of one or more fatty compounds. More preferably, the solidified gel comprises about 1.5 wt. % or less of fatty compounds. Even more preferably, the solidified gel comprises about 1 wt. % or less of fatty compounds.

The solidified gel is preferably free or essentially free from $C_1$-$C_6$ monoalcohols such as ethanol and isopropanol.

In another preferred the cosmetic kit includes a container housing the solidified gel and a shaving cap, wherein the solidified gel comprises, consists essentially of, or consists of:

(a) about 1.2 wt. % or more, preferably about 1.32 to about 3 wt. %, more preferably about 1.3 to about 2 wt. %, and even more preferably about 1.5 to about 2 wt. % of gellan gum;

(b) about 1 to about 15 wt. %, preferably about 2 to about 12 wt. %, and more preferably about 2 to about 8 wt. % of one or more polyols having from 2 to 10 carbon atoms, wherein the one or more polyols are preferably selected from ethylene glycol, propylene glycol, butylene glycol, hexylene glycol, pentylene glycol, 1,3-propanediol, diethylene glycol, dipropylene glycol, caprylyl glycol, glycerin, or mixtures thereof, wherein the solidified gel preferably includes two or more polyols, wherein one of the two or more polyols is glycerin and one or more of the additional polyols are selected from ethylene glycol, propylene glycol, butylene glycol, hexylene glycol, pentylene glycol, 1,3-propanediol, diethylene glycol, dipropylene glycol, caprylyl glycol, or mixtures thereof;

(c) about 0.5 to about 15 wt. %, preferably about 1 to about 10 wt. %, more preferably about 2 to about 6 wt. % of a plurality of surfactants, wherein the plurality of surfactants comprises, consists essentially of, or consists of:

(c)(i) about 0.1 to about 8 wt. %, preferably about 0.5 to about 5 wt. %, and more preferably about 1 to about 4 wt. % of one or more amphoteric surfactants selected from alkyl amphoproprionates, betaines, alkyl sultaines, alkyl amphoacetates, or mixtures thereof, wherein preferably, at least one of the one or more amphoteric surfactants is an alkyl amphoacetate, more preferably wherein the alkyl amphoacetate is selected from disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylamphodipropionate, disodium caprylomphodipropionate, lauroamphodipropionic acid, cocoamphodipropionic acid, or mixtures thereof;

(c)(ii) about 0.1 to about 8 wt. %, preferably about 0.2 to about 5 wt. %, and more preferably about 0.5 to about 4 wt. % of one or more nonionic surfactants, wherein the one or more nonionic surfactants are preferably selected from poloxamers; polysorbates; alkyl polyglucosides; alcohols, alpha-diols, alkylphenols or esters of fatty acids, being optionally ethoxylated, propoxylated, or glycerolated (polyglyceryl-2 isostearate); ethoxylated fatty esters; glyceryl esters of fatty acids; fatty alcohol ethoxylates; alkyl phenol ethoxylates; fatty acid alkoxylates; and mixtures thereof, wherein at least one of the one or more nonionic surfactants is preferably selected from poloxamers, wherein the poloxamers are preferably selected from poloxamer-101, poloxamer-105, poloxamer-105 benzoate, poloxamer-108, poloxamer-122, poloxamer-123, poloxamer-124, poloxamer-181, poloxamer-182, poloxamer-182 dibenzoate, poloxamer-183, poloxamer-184, poloxamer-185, poloxamer-188, poloxamer-212, poloxamer-215, poloxamer-217, poloxamer-231, poloxamer-234, poloxamer-235, poloxamer-237, poloxamer-238, poloxamer-282, poloxamer-284, poloxamer-288, poloxamer-331, poloxamer-333, poloxamer-334, poloxamer-335, poloxamer-338, poloxamer-401, poloxamer-402, poloxamer-403, and poloxamer-407, or mixtures thereof;

(c)(iii) optionally, about 0.01 to about 8 wt. %, about 0.1 to about 6 wt. %, even more preferably about 0.5 to about 5 wt. % of one or more anionic surfactants, wherein the one or more anionic surfactants are preferably selected form sulfates, acyl isethionates, acyl amino acids (such as acyl taurates, acyl glycinates, acyl glutamates, and acyl sarcosinates), alkyl sulfonates, alkyl sulfosuccinates, alkyl sulfoacetates, alkoxylated monoacids, salts thereof, and a combination thereof;

wherein the plurality of surfactants and the solidified gel is preferably free or essentially free from sulfates;

wherein the plurality of surfactants and the solidified gel is preferably free or essentially free from cationic surfactants;

(d) about 75 to about 95 wt. %, preferably about 80 to about 95 wt. %, even more preferably about 85 to about 95 wt. % of water;

(e) optionally, about 0.01 to about 10 wt. %, preferably about 0.1 to about 8 wt. %, and more preferably about 1 to about 6 wt. % of one or more miscellaneous ingredients, wherein the one or more miscellaneous ingredients are selected from preservatives, fragrances, essential oils, chelating agents, antioxidants, flavonoids, vitamins, botanical extracts, UV filtering agents, proteins, protein hydrolysates, protein isolates, fillers, composition colorants, or mixtures thereof;

wherein the composition is a solidified micellar gel of a micellar solution, the composition transparent or translucent, preferably transparent, the composition has a hardness of about 0.04 N to about 15 N, preferably about 0.1 to about 12 N, even more preferably about 1 to about 10 N at 25° C., and all weight percentages are based on a total weight of the composition.

The solidified gel preferably comprises about 2 wt. % or less of oils. More preferably, the solidified gel comprises about 1.5 wt. % or less of oils. Even more preferably, the solidified gel comprises about 1 wt. % or less of oils.

The solidified gel preferably comprises about 2 wt. % or less of one or more fatty compounds. More preferably, the solidified gel comprises about 1.5 wt. % or less of fatty compounds. Even more preferably, the solidified gel comprises about 1 wt. % or less of fatty compounds.

The solidified gel is preferably free or essentially free from $C_1$-$C_6$ monoalcohols such as ethanol and isopropanol.

In yet another preferred embodiment, the cosmetic kit comprises a container housing the solidified gel and a shaving cap, wherein the solidified gel comprises, consists essentially of, or consists of:

(a) about 1.2 wt. % or more, preferably about 1.32 to about 3 wt. %, more preferably about 1.3 to about 2 wt. %, and even more preferably about 1.5 to about 2 wt. % of gellan gum;

(b) about 1 to about 15 wt. %, preferably about 2 to about 12 wt. %, and more preferably about 2 to about 8 wt. % of two or more polyols having from 2 to 10 carbon atoms, wherein one of the two or more polyols is glycerin and the other polyols are selected from ethylene glycol, propylene glycol, butylene glycol, hexylene glycol, pentylene glycol, 1,3-propanediol, diethylene glycol, dipropylene glycol, caprylyl glycol, or mixtures thereof;

(c) about 0.5 to about 15 wt. %, preferably about 1 to about 10 wt. %, more preferably about 2 to about 6 wt. % of a plurality of surfactants, wherein the plurality of surfactants comprises, consists essentially of, or consists of:

(c)(i) about 0.1 to about 8 wt. %, preferably about 0.5 to about 5 wt. %, and more preferably about 1 to about 4 wt. % of one or more alkyl amphoacetates selected from disodium cocoamphodiacetate, disodium lauroamphodiacetate, disodium caprylamphodiacetate, disodium caprylamphodiacetate, or mixtures thereof;

(c)(ii) about 0.1 to about 8 wt. %, preferably about 0.2 to about 5 wt. %, and more preferably about 0.5 to about 4 wt. % of one or more poloxamers, wherein the one or more poloxamers are preferably selected from poloxamer-101, poloxamer-105, poloxamer-105 benzoate, poloxamer-108, poloxamer-122, poloxamer-123, poloxamer-124, poloxamer-181, poloxamer-182, poloxamer-182 dibenzoate, poloxamer-183, poloxamer-184, poloxamer-185, poloxamer-188, poloxamer-212, poloxamer-215, poloxamer-217, poloxamer-231, poloxamer-234, poloxamer-235, poloxamer-237, poloxamer-238, poloxamer-282, poloxamer-284, poloxamer-288, poloxamer-331, poloxamer-333, poloxamer-334, poloxamer-335, poloxamer-338, poloxamer-401, poloxamer-402, poloxamer-403, and poloxamer-407, or mixtures thereof;

(c)(iii) optionally, about 0.01 to about 8 wt. %, about 0.1 to about 6 wt. %, even more preferably about 0.5 to about 5 wt. % of one or more anionic surfactants, wherein the one or more anionic surfactants are preferably selected form sulfates, acyl isethionates, acyl amino acids (such as acyl taurates, acyl glycinates, acyl glutamates, and acyl sarcosinates), alkyl sulfonates, alkyl sulfosuccinates, alkyl sulfoacetates, alkoxylated monoacids, salts thereof, and a combination thereof; wherein preferably the solidified gel is free or essentially free from sulfates;

wherein preferably, the composition is free or essentially free from cationic surfactants;

(d) about 75 to about 95 wt. %, preferably about 80 to about 95 wt. %, even more preferably about 85 to about 95 wt. % of water;

(e) optionally, about 0.01 to about 10 wt. %, preferably about 0.1 to about 8 wt. %, and more preferably about 1 to about 6 wt. % of one or more miscellaneous ingredients, wherein the one or more miscellaneous ingredients are selected from preservatives, fragrances, essential oils, chelating agents, antioxidants, flavonoids, vitamins, botanical extracts, UV filtering agents, proteins, protein hydrolysates, protein isolates, fillers, composition colorants, or mixtures thereof;

wherein the composition is a solidified gel of a micellar solution, the composition transparent or translucent, preferably transparent, the composition has a hardness of about 0.04 N to about 15 N, preferably about 0.1 to about 12 N, even more preferably about 1 to about 10 N at 25° C., and all weight percentages are based on a total weight of the composition.

The solidified gel preferably comprises about 2 wt. % or less of oils. More preferably, the solidified gel comprises about 1.5 wt. % or less of oils. Even more preferably, the solidified gel comprises about 1 wt. % or less of oils.

The solidified gel preferably comprises about 2 wt. % or less of one or more fatty compounds. More preferably, the solidified gel comprises about 1.5 wt. % or less of fatty compounds. Even more preferably, the solidified gel comprises about 1 wt. % or less of fatty compounds.

The solidified gel is preferably free or essentially free from $C_1$-$C_6$ monoalcohols such as ethanol and isopropanol.

Methods of Treatment

The cosmetic kit is useful in methods for topically treating the skin. The solidified gels are particularly useful in methods for treating or cleansing the skin, especially the skin of the face. In a preferred embodiment, the solidified gel is used in a method for cleansing the skin of the face, which includes methods for removing makeup, dirt, sebum, oil, contamination, or a combination thereof. The methods include application of the solidified gel to the skin, optionally massaging the composition on the skin, and rinsing or washing the solidified gel from the skin. In a preferred embodiment, the solidified gel is applied to skin of the face upon which makeup exists, and is massaged or rubbed over the skin to dislodge and dissolve the makeup, and subsequently rinsed or washed from the skin with the dislodged and dissolved makeup. After application of the solidified gel to the skin, the solidified gel may be allowed to remain on the skin for a period of time, usually less than 5 minutes. Preferably, the solidified gel remains on the skin for about 4 minutes or less, 3 minutes or less, 2 minutes or less, or 1 minute or less, before being rinsed or washed from the skin. Before or after applying the solidified gel to the skin, the shaving cap is used to shave at least a portion of the exposed surface of the solidified gel away from a remaining mass of the solidified gel in the container.

Methods of Making

The instant disclosure is also drawn to method of making the solidified gel. Methods of making or producing the solidified gel in the form of a solidified gel include dissolving a part or all of the gellan gum in water and heating the solution to a temperature of at least 70° C. for at least 5 minutes. Additional ingredients of the solidified gel can be added or combined with the water before, after, or simultaneously with the gellan gum. Typically, all ingredients are combined to form a micellar solution before heating. The gellan gum can be added to the water and dissolved. After the gellan gum is dissolved, additional ingredients, or all additional ingredients, of the solidified gel can be added before heating and micellar solution is formed. The micellar solution is heated to a temperature of at least 70° C. for at least 5 minutes. Upon cooling, the composition forms a solidified gel that is transparent.

The gellan gum can be dissolved in the water, for example, by gentle mixing. The heat also helps to dissolve the gellan gum. In instances where additional ingredients of the solidified gel are added after dissolving the gellan gum in water, it is preferrable to add them before cooling the solution of gellan gum and water. Upon cooling, the solution solidifies making it more difficult to uniformly blend the ingredients.

The solution of gellan gum and water and additional ingredients of the solidified gel are typically heated to at least 70° C. for 5 minutes. Nonetheless, higher temperatures and longer times may be used. For example, in various embodiments, the solution of gellan gum and water (and optionally additional ingredients of the solidified gel) is heated to at least 72° C., at least 75° C., at least 78° C., or at least 80° C. In various embodiments, the solution of gellan gum and water (and optionally additional ingredients of the solidified gel) are heated to a temperature of about 70 to about 90° C., about 72 to about 90° C., about 75 to about 90° C., about 78 to about 90° C., about 70 to about 85° C., about 72 to about 85° C., about 75 to about 85° C., about 78 to about 85° C., about 70 to about 80° C., about 72 to about 80° C., or about 75 to about 80° C.

The micellar solution of gellan gum and water and optionally additional ingredients of the solidified gel are heated and typically maintained at the heated temperature for at least 5 minutes, at least 6 minutes, at least 8 minutes, at least 10 minutes, or at least 15 minutes. In various embodiments, the micellar solution is heated and maintained at the heated temperature for about 5 to about 30 minutes, about 8 to about 30 minutes, about 10 to about 30 minutes, about 5 to about 20 minutes, about 8 to about 20 minutes, or about 10 to about 20 minutes. Preferably, the micellar solution is heated to about 70 to about 85° C. for about 5 to about 20 minutes, more preferably the micellar solution is heated to about 70 to about 80° C. for about 5 to about 15 minutes.

After heating for a sufficient amount of time, the heated composition can be poured into packing or poured into a mold so that upon cooling and solidification, the solidified gel will have a predetermined shape or size. Preferably, it is poured into containers according to the instant disclosure.

EXAMPLES

Various changes can be made in the above-compositions and methods without departing from the scope of the invention. Accordingly, it is intended that the entire disclosure in the above description and in the examples given below, is illustrative and not limiting.

Example 1

Inventive Compositions

| | | | | A | B | C |
|---|---|---|---|---|---|---|
| (a) | | Thickener | GELLAN GUM | 1 | 1.5 | 1 |
| (b) | | Polyol | HEXYLENE GLYCOL | 2 | 2 | 2 |
| | | | GLYCERIN | 1 | 1 | 1 |
| (c) | (i) | Amphoteric Surfactant | DISODIUM COCO-AMPHODIACETATE | 1.4 | 1.4 | 1.4 |
| | (ii) | Nonionic Surfactant | POLOXAMER 184 | 1 | 1 | 1 |
| (e) | | Miscellaneous* | | ≤5 | ≤5 | ≤5 |
| (d) | | Water | | QS | QS | QS |
| | | Transparent | | Yes | Yes | Yes |
| | | Solidified | | Yes | Yes | Yes |

*Preservatives, fragrances, essential oils, chelating agents, antioxidants, flavonoids, vitamins, botanical extracts, UV filtering agents, proteins, protein hydrolysates, protein isolates, fillers, composition colorants, or mixtures thereof.

Example 2

Comparative Compositions

| | | | A | C-1 | C-2 | C-3 | C-4 | C-5 | C-6 | C-7 |
|---|---|---|---|---|---|---|---|---|---|---|
| (a) | Thickener | GELLAN GUM | 1 | | | | | | | |
| | Comparative Thickeners | GUAR GUM | | 1 | | | | | | |
| | | XANTHAN GUM | | | 1 | | | | | |
| | | ACACIA SENEGAL GUM | | | | 1 | | | | |
| | | SCLEROTIUM GUM | | | | | 1 | | | |
| | | DEHYDROXANTHAN GUM | | | | | | 1 | | |
| | | CORN STARCH | | | | | | | 1 | |
| | | PECTIN | | | | | | | | 1 |
| (b) | Polyol | HEXYLENE GLYCOL | 2 | 2 | 2 | 2 | 2 | 2 | 2 | 2 |
| | | GLYCERIN | 1 | 1 | 1 | 1 | 1 | 1 | 1 | 1 |
| (c) | Surfactants | DISODIUM COCO-AMPHODIACETATE | 1.4 | 1.4 | 1.4 | 1.4 | 1.4 | 1.4 | 1.4 | 1.4 |
| | | POLOXAMER 184 | 1 | 1 | 1 | 1 | 1 | 1 | 1 | 1 |
| (e) | Miscellaneous* | | ≤5 | ≤5 | ≤5 | ≤5 | ≤5 | ≤5 | ≤5 | ≤5 |
| (d) | Water | | QS | QS | QS | QS | QS | QS | QS | QS |
| | Transparent | | Yes | No (hazy appearance) | | | | | | |
| | Solidified | | Yes | No (paste/dough-like consistency) | | | | | | |

*Preservatives, fragrances, essential oils, chelating agents, antioxidants, flavonoids, vitamins, botanical extracts, UV filtering agents, proteins, protein hydrolysates, protein isolates, fillers, composition colorants, or mixtures thereof.

A variety of polysaccharide thickening agents were investigated in an attempt to generate a transparent, solidified gel. The polysaccharide thickening agents included: gar gum, xanthan gum, acacia Senegal gum, sclerotium gum, dehydroxanthan gum, corn starch, and pectin (Comparative Compositions C-1 through C-7) in addition to gellan gum (Inventive Composition A). All compositions in the table above (A and C-1 through C-7) were prepared by dissolving the polysaccharide thickening agent in water at room temperature, adding the additional ingredients of the compositions, and mixing the compositions. Subsequently, the transparency and thickness were visually assessed. None of the compositions formed a solidified gel. The compositions were subsequently "cooked" by heating them to 70° C. for 5 minutes. After cooking, the compositions were allowed to cool to room temperature. After cooling, the compositions were again visually evaluated for transparency and thickness. None of the compositions formed a transparent solidified gel other than Inventive Composition A. Instead, Comparative Compositions C-1 through C-7 were hazy/cloudy and had a paste-like or dough-like consistency-they were not solid like Inventive Composition A.

The foregoing disclosure illustrates and describes embodiments of the invention. The disclosure shows and describes only the preferred embodiments but it is understood that the invention is useable in various other combinations, modifications, and environments and is capable of changes or modifications within the scope of the inventive concepts expressed herein, commensurate with the above teachings and/or the skill or knowledge of the relevant art. The embodiments described herein above are further intended to explain best modes known by applicant and to enable others skilled in the art to utilize the inventive. Accordingly, the description is not intended to limit the invention.

As used herein, the terms "comprising," "having," and "including" (or "comprise," "have," and "include") are used in their open, non-limiting sense. The phrase "consisting essentially of" limits the scope of a claim to the specified materials or steps and those that do not materially affect the basic and novel characteristics of the claimed invention.

The terms "a," "an," and "the" are understood to encompass the plural as well as the singular.

Thus, the term "a mixture thereof" or "a combination thereof" also relates to "mixtures thereof" or "combinations thereof." Throughout the disclosure, the term "a combination thereof" may be used following a list of elements as shown in the following example where letters A-F represent the elements: "one or more elements selected from A, B, C, D, E, F, and a combination thereof." The term, "a combination thereof" does not require that the combination include all of A, B, C, D, E, and F (although all of A, B, C, D, E, and F may be included). Rather, it indicates that a combination of any two or more of A, B, C, D, E, and F can be included. In other words, it is equivalent to the phrase "one or more elements selected from A, B, C, D, E, F, and a combination of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a combination thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

The term "plurality" means "more than one" or "two or more."

Other than in the operating examples, or where otherwise indicated, all numbers expressing quantities of ingredients and/or reaction conditions can be modified in all instances by the term "about," meaning within +/−10% of the indicated number. For example, an amount of "about 1 wt." can include an amount as low as 0.90 wt. % or as high as 1.1. Similarly, an amount of "about 50" can include an amount as low as 45 wt. % and as high as 55 wt. %.

Some of the various categories of ingredients identified for the solidified gel may overlap. In such cases where overlap may exist and the solidified gel include one or more overlapping ingredients, an overlapping ingredient does not represent more than one claimed component. For example, a fatty acid may be construed as both an "oil" and separately as a "nonionic surfactant." If a claimed solidified gel refers to an oil and separately to a nonionic surfactant, a single fatty acid in the solidified gel will serve as only the oil or as only as the nonionic surfactant. A single fatty acids cannot simultaneously serve as both the oil and the nonionic surfactant.

All percentages, parts, and ratios herein are based upon the total weight of the compositions of the present invention, unless otherwise indicated.

All ranges and values disclosed herein are inclusive and combinable. For examples, any value or point described herein that falls within a range described herein can serve as a minimum or maximum value to derive a sub-range, etc. Furthermore, all ranges provided are meant to include every specific range within, and combination of sub-ranges between, the given ranges. Thus, a range from 1-5, includes specifically 1, 2, 3, 4 and 5, as well as sub ranges such as 2-5, 3-5, 2-3, 2-4, 1-4, etc.

The surfactants referred to throughout the disclosure may include those having a counter-ion such as an alkali metal, alkaline earth metal, or ammonium counterion. This list of counterions, however, is non-limiting.

The term "surfactant" (or "emulsifier") includes salts of the surfactant, to the extent they exist, even if not explicitly stated. In other words, whenever the disclosure refers to a surfactant (or surfactants), it is intended that salts of the surfactants are also encompassed to the extent they exist, even though the specification may not specifically refer to a salt (or may not refer to a salt in every instance throughout the disclosure), for example, by using language such as "a salt thereof" or "salts thereof." Sodium and potassium are common cations that form salts with surfactants. However, additional cations such as ammonium ions, or alkanolammonium ions such as monoethanolammonium or triethanolammonium ions, may also form salts of surfactants.

The term "micellar" as used throughout the disclosure is used in accordance with its ordinary and customary meaning. Along these lines, a micellar composition is a composition containing a dispersion of micelles, which are typically aggregated amphiphiles in equilibrium with free, unaggregated amphiphiles. Micellar compositions form when the concentration of amphiphile exceeds the critical micellar concentration (CMC) or critical aggregation concentration (CAC).

The solidified gel of the instant disclosure is formed by gelling (solidifying) a micellular solution. Therefore, a "solidified gel of a micellular solution" is a solid gel formed by gelling (solidifying) a micellar solution, i.e., a micellar solution is prepared and then gelled (solidified) with heat. Without wishing to be bound by a particular theory, the inventors believe the micellar structure of the solution is maintained in the solidified gel. Therefore, the composition can be referred to as a "solidified micellar gel."

The term "substantially free" or "essentially free" as used herein means the specific material may be present in small amounts that do not materially affect the basic and novel characteristics of the claimed invention. For instance, there may be less than 1% by weight of a specific material added to a composition, based on the total weight of the compositions (provided that an amount of 1% or less by weight does not materially affect the basic and novel characteristics of the claimed invention). Similarly, when a composition is essentially free from a particular element, the composition may include 1 wt. % or less, 0.5 wt. % or less, 0.1 wt. % or less, 0.05 wt. % or less, 0.01 wt. % or less, or none of the specified material. For example, if a composition is "substantially free" or "essentially free" from ethanol, the composition may optionally include ethanol in an amount up to 1 wt. %, based on the total weight of the composition, provided an amount of 1 wt. % does not materially affect the basic and novel characteristics of the composition. Furthermore, the composition may optionally include 0.5 wt. % or less, 0.1 wt. % or less, 0.05 wt. % or less, 0.01 wt. % or less, or none of the ethanol.

All components positively set forth in the instant disclosure can be negatively excluded from the claims and from the compositions and methods described throughout the disclosure. In other words, the solidified gel of the instant disclosure may be free or essentially free of any one or more of the components positively set forth in the instant disclosure.

All publications and patent applications cited throughout the disclosure are incorporated herein by reference in their entirety, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A cosmetic kit comprising:

(i) a container with an interior chamber containing a solidified gel of a micellar solution and a dispensing opening that exposes an outer surface of the solidified gel, wherein the solidified gel comprises:

(a) about 1.2 wt. % or more of gellan gum;

(b) about 1 to about 10 wt. % of one or more polyols having from 2 to 10 carbon atoms;

(c) about 1 to about 10 wt. % of one or more surfactants; and (d) about 80 to about 95 wt. % of water;

wherein the solidified gel is transparent, has a hardness of at least 2 N at 25° C., and all weight percentages are based on a total weight of the solidified gel; and (ii) a shaving cap comprising a planar surface and one or more openings through the planar surface, and one or more shaving edges along the one or more openings, for shaving at least part of an exposed surface of the solidified gel extending through the dispensing opening of the container.

2. The cosmetic kit of claim 1, wherein the one or more shaving edges shave at least part of the exposed surface of the solidified gel when the shaving cap is rotated relative to the container with sufficient force to overcome shearing resistance of the solidified gel.

3. The cosmetic kit of claim 1, wherein the one or more shaving edges comprises a beveled edge or a blade extending away from the planar surface toward the exposed surface of the solidified gel when the shaving cap is applied over the dispensing opening of the container.

4. The cosmetic kit of claim 1, wherein the one or more polyols are selected from ethylene glycol, propylene glycol, butylene glycol, hexylene glycol, pentylene glycol, 1,3-propanediol, diethylene glycol, dipropylene glycol, caprylyl glycol, glycerin, or mixtures thereof.

5. The cosmetic kit of claim 1, wherein the composition comprises glycerin and one or more additional polyols selected from ethylene glycol, propylene glycol, butylene glycol, hexylene glycol, pentylene glycol, 1,3-propanediol, diethylene glycol, dipropylene glycol, caprylyl glycol, or mixtures thereof.

6. The cosmetic kit of claim 1 comprising a plurality of surfactants, wherein the plurality of surfactants includes one or more amphoteric surfactants and one or more nonionic surfactants.

7. The cosmetic kit of claim 6, wherein the one or more amphoteric surfactants are selected from alkyl amphoproprionates, betaines, alkyl sultaines, alkyl amphoacetates, or mixtures thereof.

8. The cosmetic kit of claim 7, wherein at least one of the one or more amphoteric surfactants is an alkyl amphoacetate selected from disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylampho-dipropionate, disodium caprylomphodipropionate, lauroamphodipropionic acid, cocoamphodipropionic acid, or mixtures thereof.

9. The cosmetic kit of claim 6, wherein the one or more nonionic surfactants are selected from poloxamers.

10. The cosmetic kit of claim 1, wherein the solidified gel comprises:

(e) about 0.1 to about 10 wt. % of one or more miscellaneous ingredients.

11. The cosmetic kit of claim 10, wherein the one or more miscellaneous ingredients are selected from preservatives, fragrances, essential oils, chelating agents, antioxidants, flavonoids, vitamins, botanical extracts, UV filtering agents, proteins, protein hydrolysates, protein isolates, fillers, composition colorants, or mixtures thereof.

12. The cosmetic kit of claim 1, wherein the solidified gel comprises less than 2 wt. % of fatty compounds.

13. The cosmetic kit of claim 1, wherein the solidified gel is not an emulsion.

14. The cosmetic kit of claim 1, wherein the solidified gel is free from film forming polymers, cationic polymers, or a combination thereof.

15. The cosmetic kit of claim 1, wherein the solidified gel is prepared by combining ingredients of the solidified gel and forming a micellar solution, wherein the gellan gum is dissolved in the water of the micellar solution, heating the micellar solution to a temperature of at least 70° C. for at least 5 minutes to form a heated solution, and cooling the heated solution to form the solidified gel.

16. The cosmetic product assembly of claim 1, wherein the container further comprises a supply mechanism within the interior chamber for advancing the solidified gel toward the dispensing opening.

17. The cosmetic product assembly of claim 16, wherein the product supply mechanism comprises a twist-up advance mechanism.

18. The cosmetic product assembly of claim 17, wherein the advance mechanism comprises an elevator, an elevator screw threadably engaging the elevator, and a rotatable hand-wheel for rotating the elevator screw.

19. A cosmetic kit comprising:

(i) a container with an interior chamber containing a solidified gel of a micellar solution and a dispensing opening that exposes an outer surface of the solidified gel, wherein the container comprises a supply mechanism within the interior chamber for advancing the solidified gel toward the dispensing opening, and wherein the solidified gel comprises:

(a) about 1 to about 3 wt. % of gellan gum;

(b) about 1 to about 10 wt. % of one or more polyols selected from ethylene glycol, propylene glycol, butylene glycol, hexylene glycol, pentylene glycol, 1,3-propanediol, diethylene glycol, dipropylene glycol, caprylyl glycol, glycerin, or mixtures thereof;

(c) about 1 to about 10 wt. % of a plurality of surfactants, wherein the plurality of surfactants include:

(i) about 0.2 to about 5 wt. % of one or more amphoteric surfactants selected from alkyl amphoacetates, wherein the alkyl amphoacetates are selected from disodium cocoamphodiacetate, disodium lauroamphodiacetate, disodium caprylamphodiacetate, disodium caprylamphodiacetate, disodium cocoamphodipropionate, disodium lauroamphodipropionate, disodium caprylampho-dipropionate, disodium caprylomphodipropionate, lauroamphodipropionic acid, cocoamphodipropionic acid, or mixtures thereof; and (ii) about 0.2 to about 5 wt. % of one or more nonionic surfactants; and (d) about 80 to about 95 wt. % of water;

(e) optionally, about 0.1 to about 10 wt. % of one or more miscellaneous ingredients;

wherein the solidified gel is transparent, has a hardness of at least 2 N at 25° C., and all weight percentages are based on a total weight of the solidified gel; and (ii) a shaving cap comprising a planar surface and one or more openings through the planar surface, and one or more shaving edges along the one or more openings, for shaving at least part of an exposed surface of the solidified gel extending through the dispensing opening of the container.

20. The cosmetic kit of claim 19, wherein:

the one or more shaving edges comprises a beveled edge or a blade extending away from the planar surface toward the exposed surface of the solidified gel when the shaving cap is applied over the dispensing opening of the container; and the one or more shaving edges shave at least part of the exposed surface of the solidified gel when the shaving cap is rotated relative to the container with sufficient force to overcome shearing resistance of the solidified gel.

* * * * *